(12) United States Patent
Noyes et al.

(10) Patent No.: US 12,193,650 B2
(45) Date of Patent: Jan. 14, 2025

(54) ORTHOPEDIC ARTHROSCOPIC OPTICAL CANNULA SYSTEM

(71) Applicant: ResnENT, LLC, Bloomington, IL (US)

(72) Inventors: Willard S. Noyes, Bloomington, IL (US); Benjamin J. Gray, Portland, ME (US); Philip J. Simpson, Solana Beach, CA (US)

(73) Assignee: ResnENT, LLC, Bloomington, IL (US)

( * ) Notice: Subject to any disclaimer, the term of this patent is extended or adjusted under 35 U.S.C. 154(b) by 338 days.

(21) Appl. No.: 17/657,713

(22) Filed: Apr. 1, 2022

(65) Prior Publication Data

US 2022/0322927 A1    Oct. 13, 2022

Related U.S. Application Data

(60) Provisional application No. 63/169,366, filed on Apr. 1, 2021.

(51) Int. Cl.
*A61B 1/00* (2006.01)
*A61B 1/005* (2006.01)
(Continued)

(52) U.S. Cl.
CPC .......... *A61B 1/317* (2013.01); *A61B 1/00114* (2013.01); *A61B 1/00124* (2013.01);
(Continued)

(58) Field of Classification Search
CPC . A61B 1/317; A61B 1/00114; A61B 1/00124; A61B 1/00133; A61B 1/0052;
(Continued)

(56) References Cited

U.S. PATENT DOCUMENTS 6,068,641 A      5/2000  Varsseveld
6,394,998 B1 *   5/2002  Wallace ................. A61B 34/35
                                                          901/29
(Continued)

FOREIGN PATENT DOCUMENTS

EP      3 076 852        4/2019
WO   WO 2005/023084      3/2005
(Continued)

OTHER PUBLICATIONS

International Search Report and Written Opinion issued in PCT Application No. PCT/US2022/023055, mailed Jul. 4, 2022, in 24 pages.

*Primary Examiner* — Timothy J Neal
(74) *Attorney, Agent, or Firm* — Knobbe, Martens, Olson & Bear, LLP

(57) ABSTRACT

Implementations described herein are directed toward an improved orthopedic arthroscopy system that reduces the number of necessary arthroscopic portals while at the same time improving endoscopic visualization and instrumentation capability within the joint space. Main embodiments of the disclosed system replace the traditional rod endoscope with a rotatable, optical cannula through which instruments can be used to manipulate tissue and perform surgery. By adding the cannula rotation capability, visualization of instrument tool tip can be easily adjusted. The disclosed system would eliminate the need for unnecessary wrist rotation by the surgeon thereby making it easier to coordinate hand position while performing surgical tasks.

34 Claims, 24 Drawing Sheets

(51) Int. Cl.
   *A61B 1/015* (2006.01)
   *A61B 1/018* (2006.01)
   *A61B 1/05* (2006.01)
   *A61B 1/06* (2006.01)
   *A61B 1/317* (2006.01)

(52) U.S. Cl.
   CPC ........ *A61B 1/00133* (2013.01); *A61B 1/0052* (2013.01); *A61B 1/015* (2013.01); *A61B 1/018* (2013.01); *A61B 1/051* (2013.01); *A61B 1/0676* (2013.01); *A61B 1/00103* (2013.01)

(58) Field of Classification Search
   CPC ......... A61B 1/015; A61B 1/018; A61B 1/051; A61B 1/0676; A61B 1/00103
   See application file for complete search history.

(56) References Cited

U.S. PATENT DOCUMENTS

| | | | |
|---|---|---|---|
| 6,638,289 B1 | 10/2003 | Johnson et al. | |
| 8,870,748 B2 | 10/2014 | Kucklick | |
| 10,271,869 B2 | 4/2019 | McGuckin, Jr. | |
| 11,707,190 B1 | 7/2023 | Truckai | |
| 2007/0010823 A1 | 1/2007 | Kucklick | |
| 2008/0294192 A1* | 11/2008 | Stefan | A61B 17/1608 606/205 |
| 2011/0270293 A1 | 11/2011 | Malla et al. | |
| 2013/0085498 A1 | 4/2013 | Matusaitais et al. | |
| 2014/0005555 A1* | 1/2014 | Tesar | A61B 1/00193 600/476 |
| 2015/0196314 A1 | 7/2015 | Brannon | |
| 2017/0265879 A1 | 9/2017 | Washburn, II et al. | |
| 2018/0214171 A1 | 8/2018 | Ryan, Jr. | |
| 2019/0328217 A1 | 10/2019 | Moreau et al. | |
| 2020/0359879 A1 | 11/2020 | Cahill et al. | |
| 2020/0359996 A1 | 11/2020 | Walsh et al. | |
| 2021/0100542 A1 | 4/2021 | Magno | |
| 2023/0404617 A1 | 12/2023 | Noyes et al. | |
| 2024/0099738 A1 | 3/2024 | Browne et al. | |

FOREIGN PATENT DOCUMENTS

| | | |
|---|---|---|
| WO | WO 2006/026236 | 3/2006 |
| WO | WO 2014/065901 | 5/2014 |

* cited by examiner

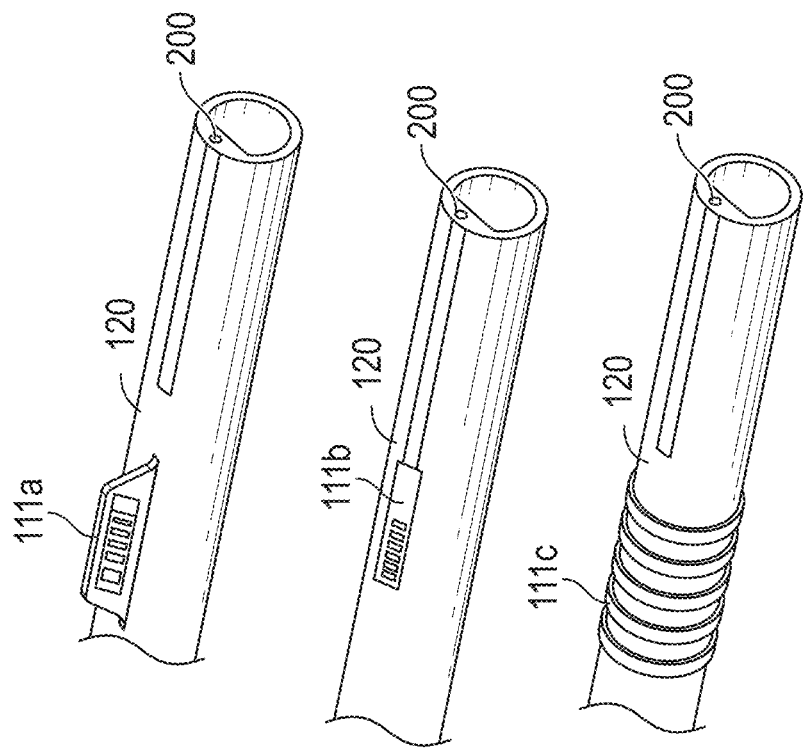
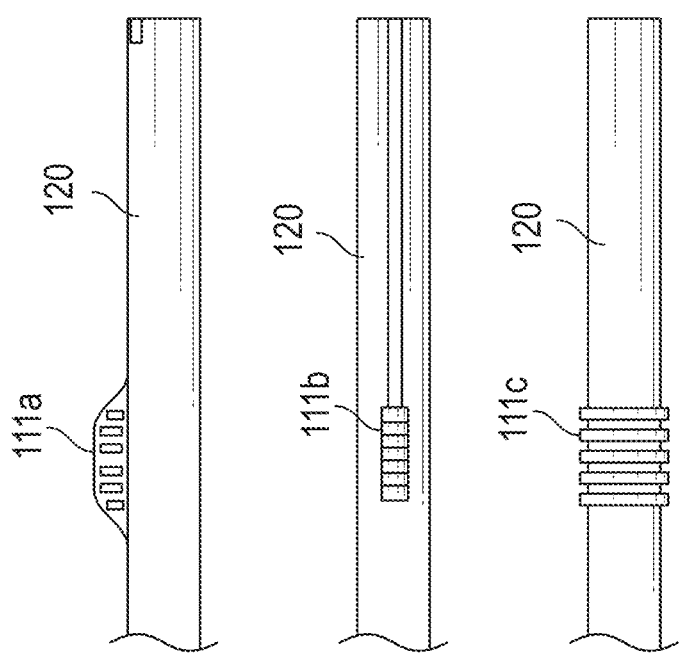
FIG. 6

ORTHOPEDIC ARTHROSCOPIC OPTICAL CANNULA SYSTEM

CROSS REFERENCE

This application claims the benefit of U.S. Patent Application No. 63/169,366, filed Apr. 1, 2021, the entirety of which is hereby incorporated by reference.

BACKGROUND

Field

This disclosure generally relates to devices, systems, and methods for arthroscopic procedures.

Related Arts

Arthroscopy is a procedure for diagnosing and treating joint problems. A surgeon inserts a small tube or cannula into a joint space through a small incision or portal. A fiberoptic or endoscopic camera is then passed through the portal and used to transmit a high-resolution image of the joint space to a video monitor. Arthroscopy allows the surgeon to see inside your joint without making a large incision. Arthroscopy is used to visualize many joints including the knee, hip, shoulder, ankle, spine, and wrist. Traditional arthroscopy uses a single portal for the endoscope and a second portal to pass instrumentation used for manipulating tissue within the joint space.

SUMMARY

Implementations described herein are directed toward an improved orthopedic arthroscopy system that reduces the number of necessary arthroscopic portals while at the same time improving endoscopic visualization and instrumentation capability within the joint space. Main embodiments of the disclosed system replace the traditional rod endoscope with a rotatable, optical cannula through which instruments can be used to manipulate tissue and perform surgery. Reusable and disposable implementations of such a system are envisioned. By adding the cannula rotation capability, visualization of instrument tool tip can be easily adjusted by rotation about a longitudinal axis of the. Conventional optically enabled spinal cannulas cannot be rotated independent of the handle. The disclosed system would eliminate the need for unnecessary wrist rotation by the surgeon thereby making it easier to coordinate hand position while performing surgical tasks. Features and aspects of the disclosed technology permit mechanized operation of instrument tools through an endoscope handle that is operated and held with the same hand. This capability frees up the other hand to rotate the cannula via a proprietary dial, thus allowing the surgeons tool operating grip and wrist position to remain stationary in a comfortable ergonomic position.

In certain implementations, the electrical wire carrying the camera signal from the cannula tip through the length of the cannula would interface via an electrical coupler (e.g., electrical commutator or service loop) that would allow at least 90 degrees of cannula rotation (or alternatively at least 360 degrees of cannula rotation or unlimited cannula rotation) without interruption of the electrical connection.

In conventional arthroscopic systems, the smaller the endoscope tip diameter, the less optical fibers are dedicated to image capture and the more are required for light delivery. Additionally, conventional spinal arthroscope technology keeps the LED light source and camera chip separate from the arthroscope handle. Light is transferred from an LED source contained within an external box through a long fiberoptic cable to the cannula. Using technology described herein, the optical camera chip (e.g., complementary metal oxide semiconductor (CMOS), charge coupled device (CCD), lens, or other type of image sensor) is placed at the tip of the arthroscopic cannula. Placement of the optical camera chip at the distal tip can enhance image resolution. This implementation-includes a LED light source contained either within the arthroscope handle or located at the tip of the cannula, thus negating the need for a standalone video rack to hold a stand-alone light source which occupies operating room space and increases equipment expense. Other embodiments of this invention provide for a multi-camera chip design with camera sensors angled slightly apart from one another in a divergent fashion. Although the angle of divergence and number of CMOS chips could vary, by utilizing this design, an instrument shaft placed through the cannula working channel can be digitally subtracted from the overall image thereby improving joint space visualization without the need for instrument shaft removal. Alternatively, integrating multiple camera chips at different angles could allow for a split screen image of the joint space to be presented on the monitor, head mounted display, or portable display device. In other embodiments, through the use of AI (artificial intelligence) technology, multiple 2D images obtained from multiple cameras located at the tip of the cannula could be used to create 3D image or virtual reality representations of an anatomic joint space.

The disclosed embodiments herein allow for two types of instrumentation approaches through the optical cannula. The first method involves passing an instrument through the optical cannula from proximal-to-distal. The tool tip in this scenario must remain smaller than the working channel diameter in order to effectively advance the instrument through the cannula. The second method allows for a removable instrument shaft (with distally attached tool tip) to be advanced distal-to-proximal through the cannula. In both scenarios, the proximal end of the tool shaft could be made to engage a portion of a mechanized handle in a manner that permits the surgeon to operate the tool tip attached the distal end of the instrument shaft by squeezing a lever incorporated into the design of the endoscope handle. For those instrument shafts passed from distal-to-proximal, the tool tip can remain larger than the working channel of the cannula thus allowing for greater tool options for a particular surgical application. In some embodiments, the mechanized endoscopic handle would remain in a straight-line orientation to the instrument shaft and allow for an overhand surgeon grip. In other implementations, the endoscope handle may be offset from the long axis of the optical cannula and instrument shaft thereby allowing a surgeon to hold the device in for more of a "pistol grip" fashion. In certain instances, it may be advantageous to utilize traditional arthroscopic forceps (with handles already attached and tool tip size small enough to pass through the disclosed optical cannula). In these scenarios, there would be no need for the mechanized handle portion of the disclosed device. Although most arthroscopic systems currently on the market enable instruments to be passed therethrough, current systems, however, do not have the option of both a passive and active method for instrument engagement and are therefore limited in their surgical application.

Another feature of this invention involves a means by which to maintain the ordered, stationary positioning of the electrical, suction and irrigation hoses off the back of the endoscope handle during surgery. Embodiments of this system utilize a disposable suction/irrigation harness that removably or permanently fits around the cannula in a watertight fashion. Within this harness are circumferential fluid and/or suction chambers that line up with corresponding holes or ports placed through the outer wall of the optical cannula. Inside the cannula, these holes communicate with the suction and irrigation spaces or channels formed between the instrument shaft and cannula wall. In some embodiments, the holes are offset from one another along the circumference of the outer cannula so as to separate the two fluid channels as much as possible. Cannula embodiments that use the inserted instrument shaft rather than an integrated working channel within the cannula to form the fluid channels would maximize the inner diameter of the cannula for passage of larger, rigid or flexible instrument tips, shafts, and micro-debriders. Applying these or similar implementations allow suction and irrigation capabilities to remain constant even during cannula rotation. The perpendicular or angled orientation of traditional side suction/irrigation ports seen with existing arthroscopic cannula systems would therefore be eliminated. By utilizing this methodology, all hoses and the endoscope cord would remain in stable position even while the cannula is rotated. The hoses and cords could therefore be grouped together and secured in a streamlined bundle off the back of the device thereby improving clutter within the operative field.

In some implementations, the endoscope handle and cannula along with incorporated optics and irrigation/suction channels may be disposable. In these implementations, the electrical coupler connecting the cannula camera wire to the endoscope handle might be housed or included within the suction/irrigation harness along with slack wire (i.e., service loop) to permit rotation of the cannula. In other implementations, the endoscope handle may be reusable, but encased in a manner that would allow for easy cleaning and sterilization. In other embodiments, individual system parts and optical interfaces may be either disposable or reusable. If the optical cannula and endoscope handle are configured for reusable use, the electrical connection might utilize circumferential electrical contact leads or bands around the outer cannula perimeter (i.e., commutators). Still other electrical contact methods to allow free rotation are contemplated. Regardless of reusability, all individual components of the disclosed system would combine in a manner that is intuitive and easy to assemble, disassemble, and clean/sterilize.

In still other embodiments, the optical, rotatable cannula could be articulating. The direction and angle of articulation could vary, but may be uni-directional or multi-directional with angulation anywhere between zero and 180 degrees. Activation of the articulation might involve a dial, a lever, a telescoping mechanism, a robotic mechanism, or some other integrated means incorporated within or attached to the endoscope handle or optical forceps system. Such a mechanism would nearly eliminate the need to lever the cannula in order to access poorly visualize areas of the joint space. This in turn would serve to minimize tissue damage and instrument breakage. An articulating cannula would further enable and expand the use of flexible instrument shafts and micro-debriders. Such an advancement could be applied to other surgical specialties including but not limited to ENT, neurosurgery, general surgery, urology, OB/GYN, plastic surgery, podiatry, veterinary, etc. In some implementations one or more notches might be incorporated into the side or tip of the cannula to permit facilitated articulation of the instrument shaft as it exits the distal cannula.

The foregoing summary is illustrative only and is not intended to be limiting. Other aspects, features, and advantages of the systems, devices, and methods and/or other subject matter described in this application will become apparent in the teachings set forth below. The summary is provided to introduce a selection of some of the concepts of this disclosure. The summary is not intended to identify key or essential features of any subject matter described herein

BRIEF DESCRIPTION OF THE DRAWINGS

The present disclosure, in accordance with one or more implementations, is described in detail with reference to the following figures. The figures are provided for purposes of illustration only and merely depict example implementations. Furthermore, it should be noted that for clarity and ease of illustration, the elements in the figures have not necessarily been drawn to scale.

Some of the figures included herein illustrate various implementations of the disclosed technology from different viewing angles. Although the accompanying descriptive text may refer to such vies as "top," "bottom," "frontal," "rear," or "side" views, such references are merely descriptive and do not imply or require that the disclosed technology be implemented or used in a particular special orientation unless explicitly stated otherwise.

FIG. 6 shows examples of electrical couplers for image data transmission in accordance with implementations of the disclosure.

DETAILED DESCRIPTION

Figure 1:
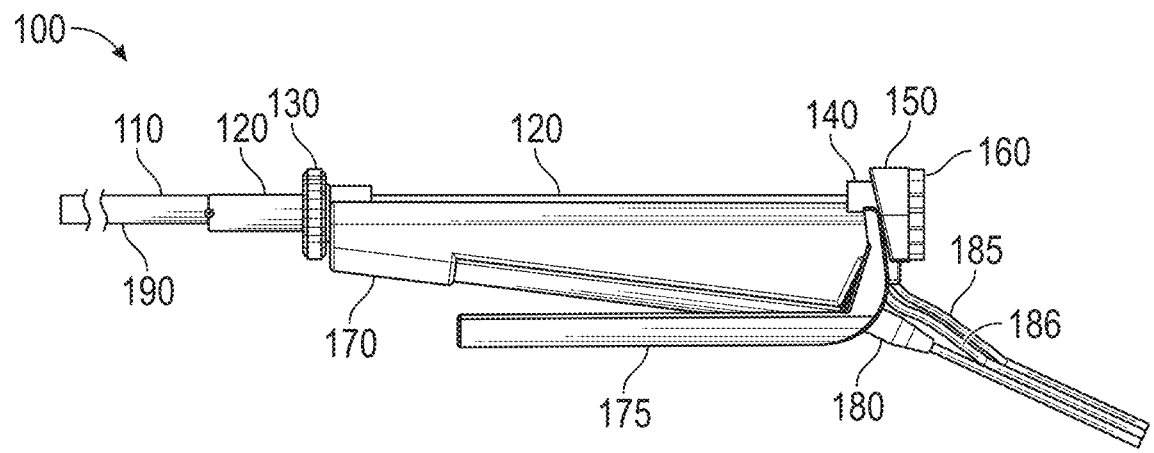
FIG. 1 shows a side view of the optical cannula system.

The various features and advantages of the systems, devices, and methods of the technology described herein will become more fully apparent from the following description of the examples illustrated in the figures. These examples are intended to illustrate the principles of this disclosure, and this disclosure should not be limited to merely the illustrated examples. The features of the illustrated examples can be modified, combined, removed, and/or substituted as will be apparent to those of ordinary skill in the art upon consideration of the principles disclosed herein.

Arthroscopy is a procedure for diagnosing and treating joint problems. A surgeon inserts a small tube or cannula into a joint space through a small incision or portal. A fiberoptic or endoscopic camera is then passed through the portal and used to transmit a high-resolution image of the joint space to a video monitor. Arthroscopy allows the surgeon to see inside your joint without making a large incision. Arthroscopy is used to visualize many joints including the knee, hip, shoulder, ankle, spine, and wrist. Traditional arthroscopy uses a single portal for the endoscope (with or without irrigation and suction) and a second portal to pass instrumentation used for manipulating tissue within the joint space. A current trend in the surgical orthopedic marketplace is the miniaturization of arthroscopes and associated instrument forceps. Newer arthroscopic systems such as the Nanoscope system produced by Arthrex uses a very small endoscope cannula in one portal and a second portal to pass miniaturized forceps used for tissue manipulation through a second portal.

Smaller incisions and fewer portals allow for improved patient comfort, lower cost, decreased operative time, and the capability of performing arthroscopic procedures in the office rather than in the hospital or ambulatory surgery center setting. Until recently, few systems have even contemplated visualizing and manipulating tissue through a single portal. The Stryker SPA system uses a dual cannula device that is inserted through a single portal incision. Unfortunately, that portal is made large to accommodate both cannulas, one for the endoscope and the other for a powered micro-debrider. Having to manipulate two cannulas through a single portal is technically difficult.

Arthroscopy generally requires irrigation fluid and suction in order to clear debris and inflate the joint for improved visualization. Suction and irrigation hoses attach to connectors on the outside of the rigid cannula through which the endoscope is passed. These hoses are oriented perpendicular to the long axis of the cannula and extend sideways off of the cannula thereby adding to surgical clutter on the field and surgeon frustration during the procedure. The camera head cable and fiberoptic light cable further add to the number of cables and hoses intertangled and within the surgical field. When using a powered suction micro-debrider through a second portal, two more cables/hoses are added to the mix. As such, it is not common for there to be six hoses/cords all competing for space within the operative field. Because the surgeon must rotate and twist the scope during the procedure to improve visualization, the hoses often get tangled and twisted making the case more difficult and frustrating for the surgeon and scrub nurse.

Conventional arthroscopy used standard rod fiberoptic endoscopes for visualization. These endo scopes have distal tips that can visualize at different angles depending on the endoscope. Some examples include zero, thirty, seventy-degree rigid endoscopes. When endoscopes having angled fields of view are passed into a joint space, the surgeon must rotate the scope along its horizontal axis in order to visual the entire joint space. The surgeon must also lever the rod of the scope in a multitude of directions in order to capture a larger visual field. This rocking or levered manipulation of the scope as it passes through the portal can result in greater trauma to the incision site and joint space not to mention damage to the scope and increased surgeon fatigue.

Traditionally only a single instrument can be passed through an arthroscopic portal at one time. Some spinal arthroscopic systems are beginning to utilize single, rigid fiberoptic cannulas through which instruments can be passed (JOIMAX® minimally invasive spinal surgery). These systems utilize fiber optic strands to carry the image from the joint space through the cannula to the camera head CMOS chip that is attached to the proximal end of the instrument cannula. This results in an image quality that is potentially limited by the number of optical fibers delivering the image to the CMOS sensor. With the improvements in the miniaturization and resolution of CMOS chip technology, an endoscope camera/CMOS chip that is located at the tip of the cannula would be advantageous. Likewise, these optical spinal cannulas require rotating the entire handle in order to change the viewing angle or view around an instrument shaft. Such an action causes the hoses and cords that come off the handle to flop around the back of the handle while the cannula is being turned. These cannulas are also larger in diameter and in all instances require instruments to be passed through the cannula from proximal-to-distal and be operated by a second hand.

In some orthopedic arthroscopic procedures, a second instrument is required to effectively manage a surgical task.

Should a second instrument be required, it becomes necessary to create a third incision/portal to accommodate the second instrument. This adds to surgical time, tissue injury, and patient discomfort. It is apparent that any means by which a surgeon can improve image resolution, limit the number of surgical portals, decrease incision size, reduce the need for endoscope rotation and/or levering, and minimize the number of surgical cords/hoses on the operative field would be a beneficial and welcomed advancement for the worldwide surgical marketplace.

As noted previously, current implementations of orthopedic arthroscopic cannulas, arthroscopic instruments, and arthroscopic endoscopes (arthroscopes) have limitations with respect to the ability to operate and visualize through a single portal and cannula. Current systems are cumbersome, difficult to set-up, require expanded video and stacked accessory components to operate, and are not integrated in a user-friendly manner. Other limitations of current arthroscopic systems include limited visualization within the joint space, need for levering of the arthroscope to access different portions of the joint space, need for a second or third incision/portal for instrument access, suction hose, irrigation tubing, and electrical cable management, awkward hand/wrist positioning for the surgeon, and the inability to rotate the camera orientation with respect to the instrument shaft and tool tip (and vice-versa).

To this end, implementations of this disclosure are directed to an improved arthroscopic system design that corrects these current deficiencies while at the same time reducing the number of necessary portals required for a particular procedure. In effect, implementations of this disclosure allow the surgeon to free-up one hand and at least one surgical portal. In so doing, the surgeon can manipulate the extremity with one hand while visualizing and using mechanical instrumentation with the other. The rotational cannula design enables the image angle to be changed without having to turn the whole wrist or endoscopic handle. In this simplified and ergonomic manner, physician fatigue is improved and tasks that usually require a second assistant are minimized. Additionally, operative time is decreased, patient comfort is increased, fewer parts require sterilization, optical clarity is improved, and the overall cost of the procedure is reduced. Implementations of the disclosed system also allow the surgeon to perform instrumentation with tools that are larger than the diameter on the optical cannula while at the same time maintaining optical visualization of the tool tip. The disclosed implementations herein present a better "mouse trap" and improved options for surgical instrumentation and visualization during arthroscopy. Very importantly, implementations of this device will make it easier to transition surgical procedures out of the hospital and ambulatory care centers and into the physician office, thereby decreasing facility and anesthesia costs and improving surgeon efficiency and patient satisfaction.

Figure 2:
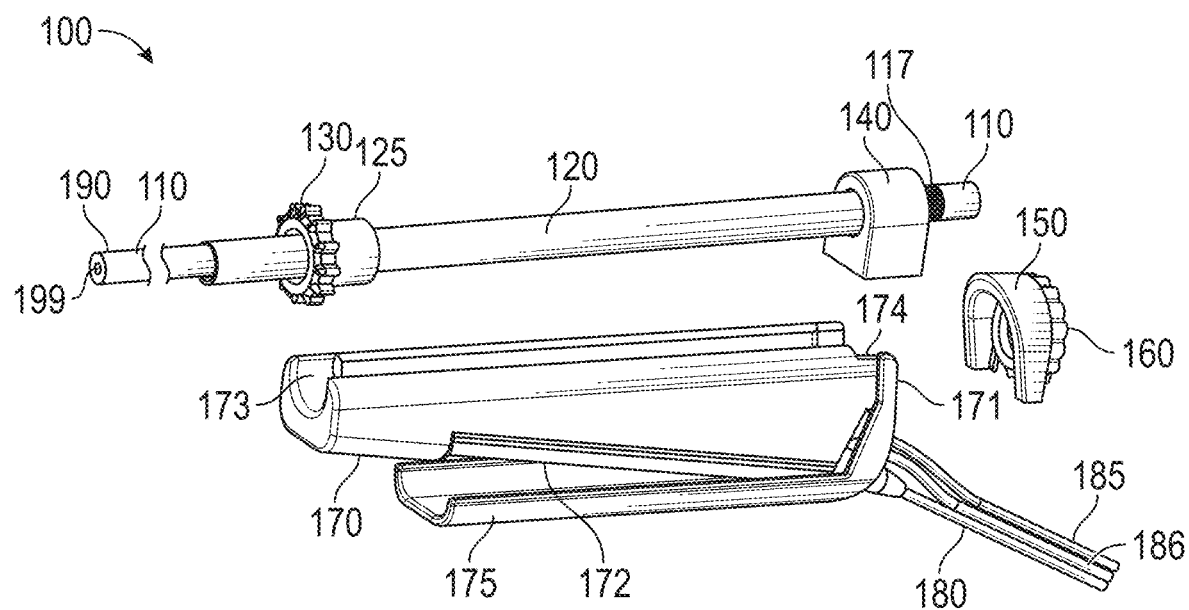
FIG. 2 shows a blow-up view of the optical cannula system shown in FIG. 1.

FIGS. 1-2 illustrate implementations of a rotatable, optical cannula system 100 in accordance with the disclosure. As illustrated in FIG. 1-2, the optical cannula system 100 may include a reusable or disposable cannula 120 with an outer turn dial 130. The cannula fits into an elongate, semicircular indentation (FIG. 10A, 178) located on the top surface of the endoscope handle 170. The turn dial 130 has a collar extension 125 that likewise snaps into a molded indentation (FIG. 2, 173) within the inner surface of the distal endoscope handle 170. When attached to the endoscope handle, rotation of the turn dial 130 causes the optical cannula turn in either clockwise or counterclockwise in a circumferential fashion. On the proximal end of the cannula 120 there is a located a suction/irrigation harness 140 that is permanently or removably attached to the optical cannula 120. The cannula can turn freely within the irrigation harness when secured to the endoscope handle. Within the proximal aspect of the endoscope handle 170 there is a molded indentation designed to receive the irrigation harness 140 utilizing a "snap-in" mechanism or alternative means such as magnets, clips, clamps, grooves, or other means not limited to the implementations described herein. Not depicted in FIG. 1-2 is an electrical coupler located along the bottom surface of the irrigation harness 140 and a separate mating electrical coupler within the proximal molded indentation 174 of handle 170 (see FIG. 10A, 177).

In certain implementations, a removable lever 175 is attached to the endoscope handle 170. Along the proximal aspect of the lever there are bilateral extensions 171. These lever extensions engage a removable locking key 150 that is designed to integrate with the back end of an instrument shaft 110. The instrument shaft 110 is comprised of an inner shaft 199 and an outer shaft 190. Movement of the inner instrument shaft within the outer shaft causes the mechanized movement of the tool tip attached to the end of the instrument shaft 110 (not depicted). Hinged movement of the lever against the endoscope body causes the locking key to reversibly move the inner instrument shaft in a direction opposite from the outer instrument shaft. In so doing, the tool tip is actuated. In certain scenarios when the mechanized aspects of the endoscope handle are not required, the instrument lever can be removed or snapped into a conforming indentation molded into the body of the endoscope handle 172. Securing the lever 175 into the handle indentation 172 could be facilitated by a magnet or alternative mechanism depending on the implementation.

On the back of the locking key 150 there is a rotatable instrument shaft turn dial 160 that engages internally with a small circular gear 117 formed within a small horizontal segment of the outer instrument shaft 110. The instrument shaft turn dial 160 rotates independently from the locking key 150. When the locking key 150 is fully engaged, the gear projections within the inner circumference of the turn dial engage the gear projections on the outer instrument shaft in a manner that allows for easy rotation of the instrument shaft as it exits the proximal end of the optical cannula. Rotation of the instrument shaft is thereby independent of the optical cannula rotation performed by rotating a separate turn dial 130 located on the opposite, more distal end of the cannula.

A removable endoscope electrical cable 180 is shown to connect to the proximal undersurface of the endoscope handle 170. Suction and irrigation hoses 185 attach to the undersurface of the suction/irrigation harness (FIG. 11c). Various embodiments of how the suction and irrigation hoses interact with the suction/irrigation harness 140 are envisioned and described later herein. It is apparent however that the streamlined orientation of all electrical cables and suction/irrigation hoses is favorable when compared to current systems.

Figure 3:
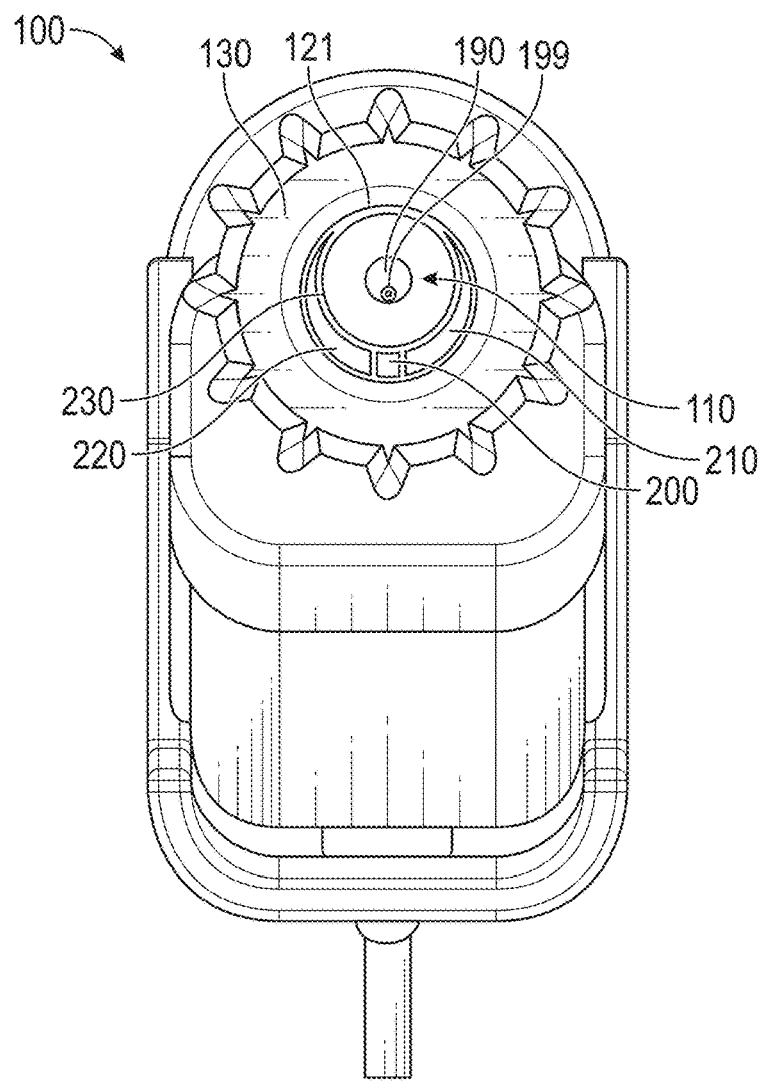
FIG. 3 shows a frontal view of the optical cannula system of FIG. 1.

FIG. 3 shows a frontal view of the disclosed optical cannula system 100. FIG. 3 highlights the internal features of the optical cannula 120. In this implementation, a single camera CMOS chip 200 is seen just inside the periphery of the cannula. It is important to note that in these implementations the camera chip is located at the distal tip of the cannula and not inside a separate camera head attached to the proximal end of the cannula or endoscope handle. Positioning of the CMOS sensor at the tip of the cannula negates any loss of image resolution seen with conventional systems that use limited optical fibers to carry the image to a distal sensor. As imaging technology advances and the size of CMOS chips get smaller and resolution improves, the implementations of the disclosed system will show progressive quality improvement of displayed images when compared to systems that use conventional fiberoptic technology.

FIG. 3 shows irrigation 210 and suction 220 channels oriented peripherally within the lumen or cannula 120. These irrigation and suction channels are carried horizontally along the length of the cannula and eventually end in holes in the outer cannula that communicate with fluid chambers located within the irrigation/suction harness 140 situated along the back end of the cannula. The optical cannula irrigation and suction channel borders are formed by the instrument shaft 110 and/or instrument working channel internally 230, the optical cannula wall 121 externally, and the CMOS chip and optical light fibers 200 centrally. In other implementations, an LED emitter placed next to the CMOS chip might be used instead of optical fibers. In some implementations, there may not be a discrete internal working cannula that is incorporated into the central lumen of the outer cannula and in other implementations the instrument shaft alone could act as the internal border for the cannulas' irrigation and suction channels.

Figure 4:
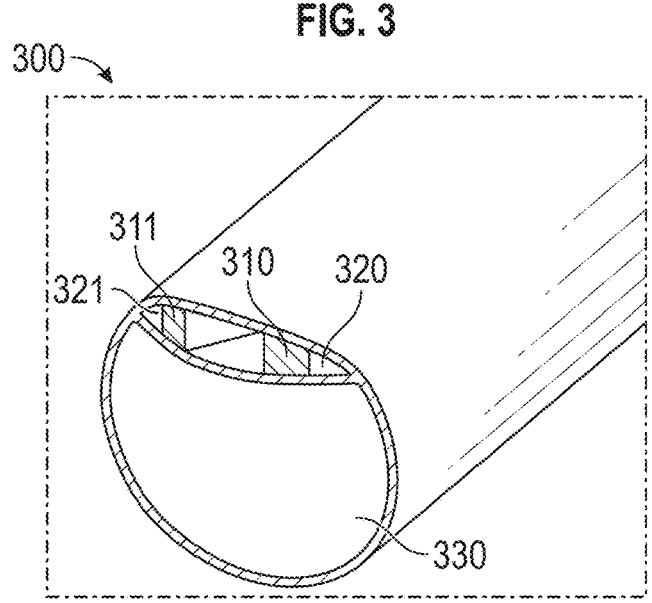
FIG. 4 shows a perspective view of a dual camera cannula embodiment of FIG. 1

FIG. 4 shows a perspective view of a dual camera chip optical cannula 300, which can be one implementation of the cannula 120. Small gaps 320, 321 laterally adjacent to the CMOS chips 310, 311 could be used to accommodate the optical light fibers or LED emitters necessary for joint illumination. By utilizing two separate CMOS chips in a divergent orientation, both camera images could be displayed individually or side by side on a split image monitor. Each image would provide a different viewing angle of the anatomical landscape. Alternatively, the images could be digitally combined or "stitched" together in a manner that would create a larger, panoramic field of view. In this implementation, the CMOS chips of optical cannula embodiment 300 are oriented 30 degrees divergent from center. Cannula systems with varying angles of camera chip divergence using two or more camera CMOS chips are envisioned. By incorporating multiple camera chips into the tip of the cannula, multiple areas of the joint space could be visualized simultaneously and displayed in a compartmentalized, 3D, or panoramic fashion on a monitor display. Conventional arthroscopic systems have limited fields of view confined by the angulation of the rigid scope lens.

Figure 5:
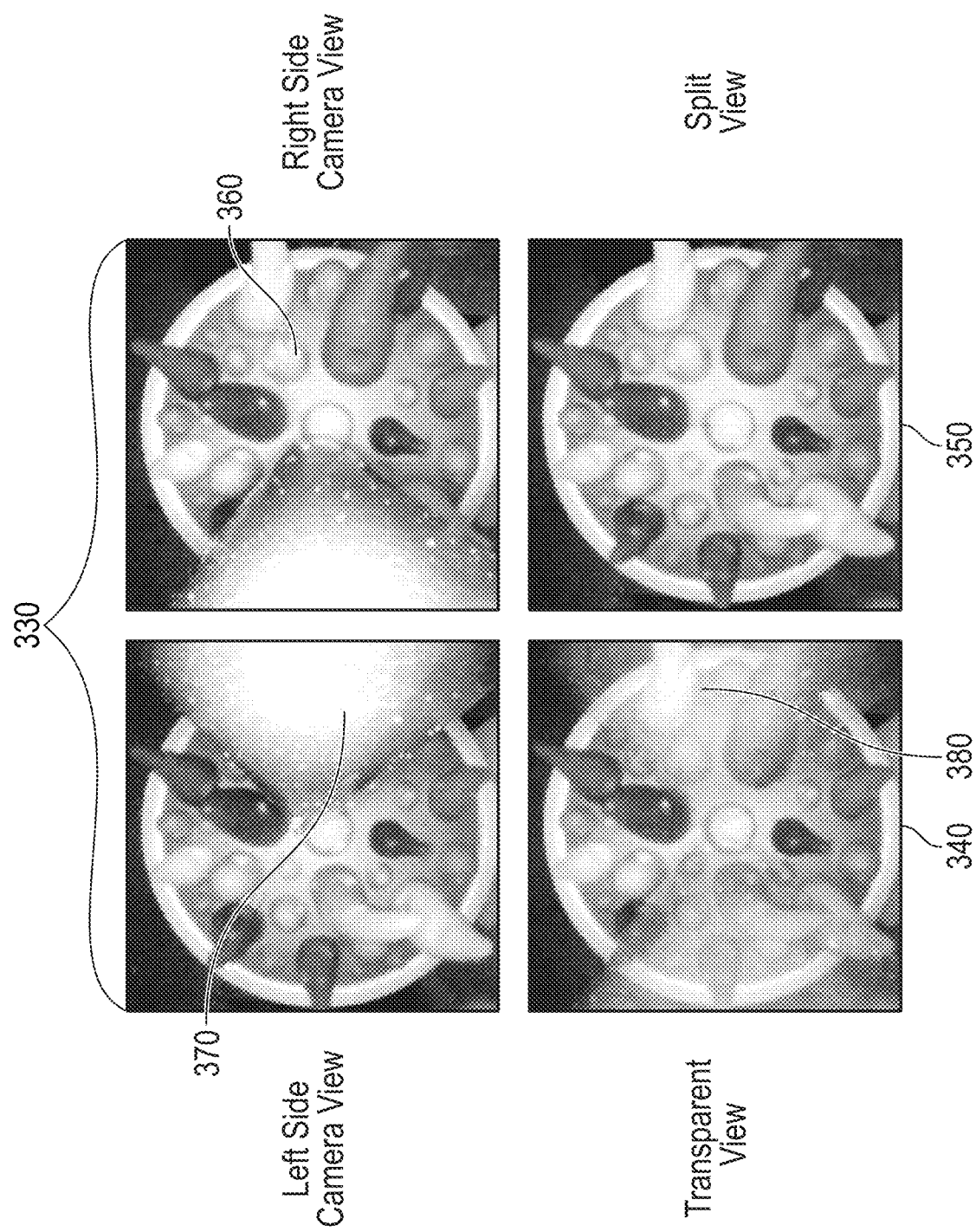
FIG. 5 shows examples of image cancellation obtained from the dual camera cannula of FIG. 2

FIG. 5 shows an example diagrammatic representation of image cancellation using a dual camera chip cannula configuration. In this application, computerized digital manipulation of the combined CMOS camera images allows for display cancellation/removal of the instrument shaft occupying the central aspect of the operative view. Split screen images 330 of two unaltered pictures created by divergent CMOS sensors are located on the top of the diagram. The visualized object 360 is obscured by the instrument shaft 370 noted centrally along the inner aspect of each top picture. The lower left picture 340 combines the digitally manipulated pictures into a single picture in a manner that shows a transparent, but still visible outline of the instrument shaft 380. The lower right picture 350 shows a digitally enhanced image with the instrument shaft completely removed from the scene. The photographed object remains visually complete as if the instrument shaft was never there. One can see how image cancellation technology could be used to improve joint space visualization during a reduced portal surgical procedure by digitally removing and reinserting the instrument shaft from the displayed image without actually removing the instrument shaft from the joint space.

FIG. 6 shows various implementations of how the rotatable, optical cannula 120 could interact with a stationary electrical couplers 111a, 111b, 111c embedded within an endoscope handle 170. The stationary electrical couplers 111a, 111b can include contacts to which wires can be attached (e.g., with a service loop connection with the cannula 120) to provide continuous electrical contact with the shaft 110 and camera chip 200. The stationary electrical coupler 111c can include circumferential contacts which form part of a commutator. Another portion of the cannula system (e.g., endoscope handle 170) can include contacts aligned with each of the circumferential contacts to provide continuous electrical contact with the shaft 110 and camera chip 200.

Figure 7:
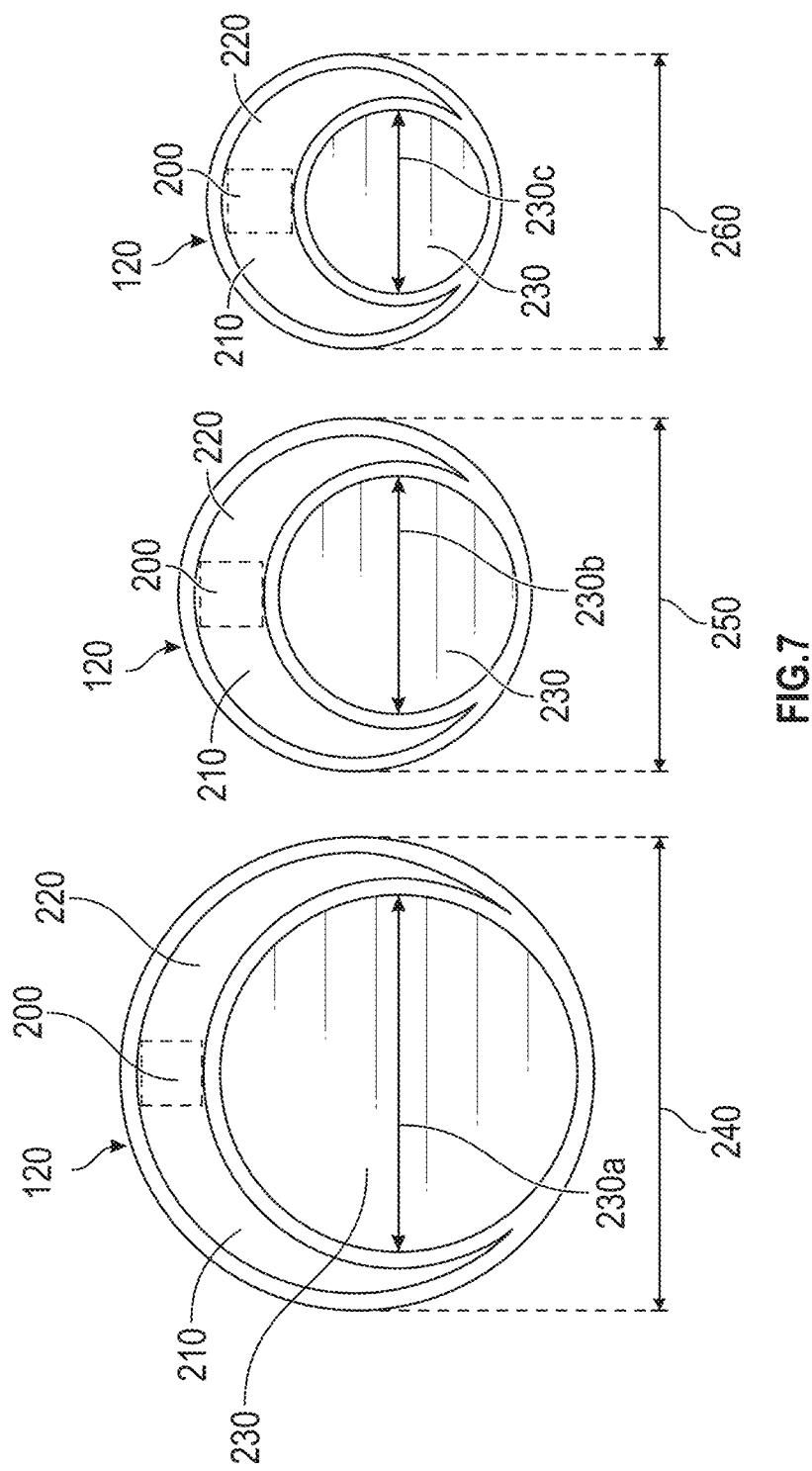
FIG. 7 shows a frontal view of an optical cannula containing a camera chip and the resultant spatial relationships from its position with the cannula.

FIG. 7 shows a visual representation of how a one-millimeter camera chip 200 can affect the size of the inner working channel 230, irrigation channel 210, and suction channel 220 of an optical cannula. A cannula 120 with outer diameters 240a of 8 mm, a working channel 230 with diameter 230a of 6.1 mm, an outer diameter 250 of 6 mm, a working channel 230 with diameter 230b of 4.1 mm, an outer diameter 260 of 4 mm, and a, working channel 230 with diameter 230c of 2.1 mm are respectively included for comparison.

Figure 8:
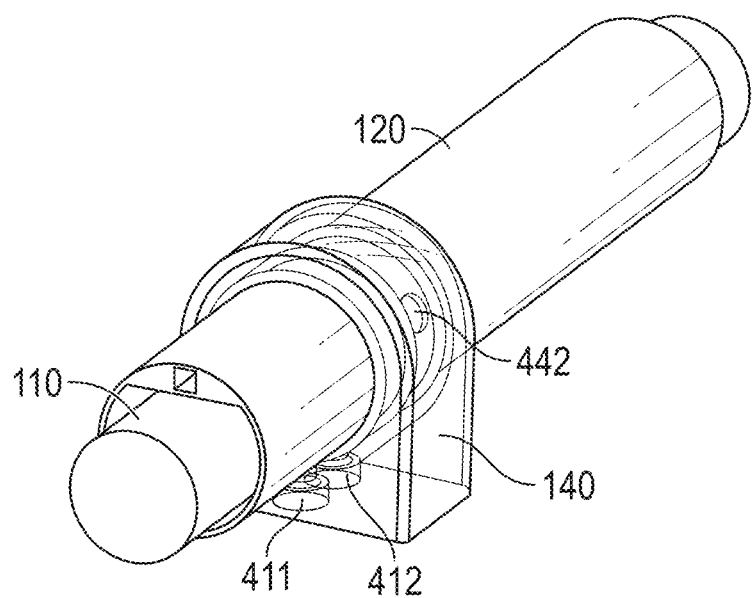
FIG. 8 shows a perspective view of the optical cannula of FIG. 1 along with its attachment to a suction/irrigation harness, in accordance with implementations of the disclosure.
Figure 9:
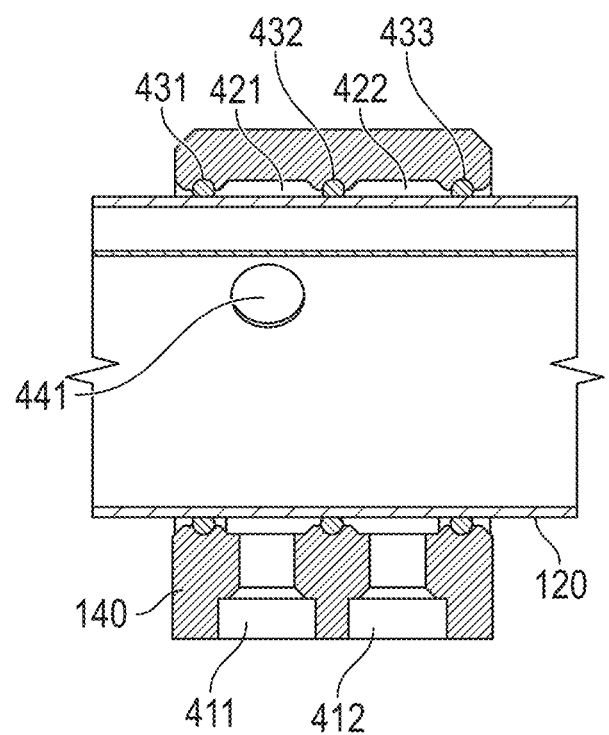
FIG. 9 shows a sagittal view through the cannula and suction/irrigation harness depicted in FIG. 8.

Conventional arthroscopic cannulas typically require suction and/or irrigation ports that are integrated into the side wall of the cannula. These ports typically have shut-off valves/levers that regulate the flow of fluid through the cannula. Often these ports are oriented between 30 and 90 degrees away from the longitudinal axis of the cannula. Implementations of the disclosed system use an alternative means for directing suction and irrigation into and out of the cannula. FIGS. 8-9 show respective transparent and sagittal views of a suction/irrigation harness 140 interacting with the optical cannula 120.

Instead of using fixated ports on the sides of the cannula, the disclosed cannula system 100 takes advantage of the rotational nature of the cannula and uses two independent fluid ports 411, 412 to drain two separate fluid or suction channels 421, 422, respectively, located within the interior circumference of the harness 140. A series of rubber seals 431, 432, 433 separate the two harness channels from one another and maintain a watertight seal against the cannula wall. A first port 441 within the outer cannula wall lines up with one of the channels inside of the suction/irrigation harness 140 and provides fluid or suction access between either the suction or the irrigation channel 210 or 220 spaced within the cannula interior. A second port 442, which may be offset longitudinally and/or circumferentially from the first port 441, provides access to the second harness chamber 422. By offsetting the ports within the cannula wall and separating the harness channels, the suction and irrigation channels remain separate from one another. When the optical cannula 120 is rotated, ports 441, 442 maintain communication with the corresponding interior fluid channels 421, 422 of the harness 140 during the rotation.

In some embodiments, there may be a rubber seal or projection attached to the outer cannula wall that lines up with one or more of the channels within the suction/irrigation harness. When the cannula is rotated into a specific circumferential position, these projections/seals could be used to seal the irrigation or suction ports 411, 412 and prevent further fluid movement through that respective port. Alternatively, a more traditional valve mechanism could be incorporated into or just outside of the harness ports 411, 412 perhaps by a mechanical extension off of the port opening thus regulating fluid inflow or egress in a more traditional manner. Other methods of regulating fluid and suction flow through the harness ports are contemplated.

Figure 10A:
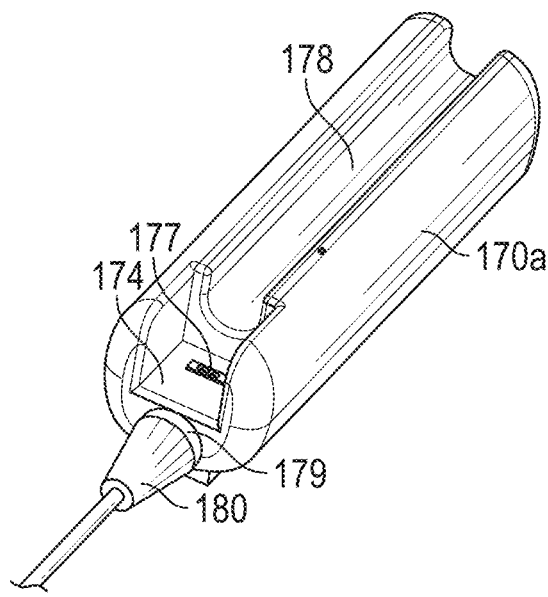
FIG. 10A shows a perspective view of an endoscope implementation with electrical cable attached.

One aspect of the optical cannula system 100 described herein is unique when compared to conventional arthroscopic systems because it combines rotational cannula optics, mechanical activation of tool tips, suction irrigation, and a fully integrated endoscope into a single hand-held device. FIG. 10A shows a simplified schematic highlighting of one alternative endoscope handle 170a with an electrical cable 180 attached to a receiving coupler 179. The endoscope handle 170a has a molded cutout 174 (e.g., rectangular) incorporated into the endoscope housing meant to receive the irrigation/suction harness 140 described in FIGS. 8-9. An electrical pathway may be provided for transmitting the image data from the camera chip located at the distal end of the cannula, through the length of the cannula to a slack wire within the suction/irrigation harness (not shown). The slack wire (not shown) connects to an electrical coupler located on the flat undersurface of the harness which contacts an endoscope coupler 177 located on the bottom of the endoscope harness cutout 174. The electrical coupler can include an image processing module that receives the signal through the slack wire (or commutator). The image processing module can be disposed within the handle 170a (e.g., internally). The electrical coupler can also be connected with the endoscope coupler 177. Accordingly, the handle 170a can be reusable to reduce costs of the assembly. Alternatively, the image data then transmits through the endoscope coupler 177 to the electrical cable 180 receiving coupler 179 and then to the endoscope cord which transmits the signal to an image processing control board located off of the operative field.

Figure 10B:
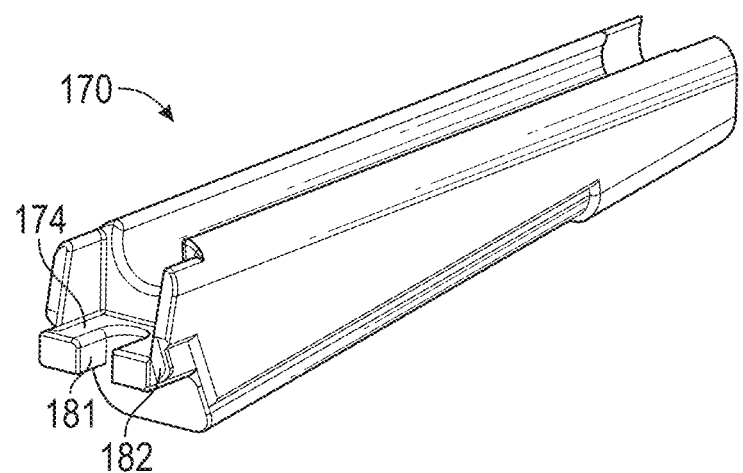
FIG. 10B shows a perspective view of a more detailed endoscope handle highlighting the various cutouts and indentations designed to fit various other components of the optical cannula system 100.

FIG. 10B shows a more detailed representation of an endoscope handle embodiment shown without the electrical connectors. A curvilinear cutout 181 is seen within the base of the harness indentation 174 that allows suction and irrigation tubes to pass through the bottom of the endoscope handle. This spatial relationship between the endoscope handle and the cords exiting the suction/irrigation harness is better appreciated in FIGS. 11-12. The suction/irrigation tubes 185, 186 can depart the endoscope handle in an orientation that allows for the tubes and electrical cable 180 to exit the device in a parallel, streamlined fashion (FIG. 12, 186). In one implementation, two semicircular indentations 182 may be incorporated into side projections along the outer base of the harness indentation 174. These indentations would receive small circular projections (not shown in the diagram) located along the medial aspect of the lever extensions (FIG. 2, 171) along the back end of the endoscope lever 175. The projections would be located in the mid aspect of the lever extension and not at the very end of the extension. Small circular projections would act to anchor the lever to the endoscope handle while at the same time allowing the lever 175 to hinge off of the proximal aspect of the endoscope handle.

Certain implementations and embodiments of the disclosed system allow for mechanical activation of instrument tool tips. Any of a variety of tool tips may be attached to an instrument shaft. For instrument tool tips that are too large to pass through the inner diameter of the optical cannula working channel, shafts could be inserted from distal-to-proximal into the optical cannula. Conversely, if the instrument tool tip is small enough to pass through the cannula, then the instrument shaft could be passed from either proximal-to-distal, or distal-to-proximal. In either instance, the intent is to work the instrument tool tip by the lever mechanism incorporated into the endoscope handle. Prior art has demonstrated means by which a mechanized handle can operate interchangeable tool tips and instrument shafts in a manner utilizing two integrated sliding instrument shafts, one inside the other. The outer circular shaft has a central channel through which a smaller diameter shaft can move back and forth. The movement interaction between the two instrument shaft components enables the tool tip to be opened and closed.

Figure 11:
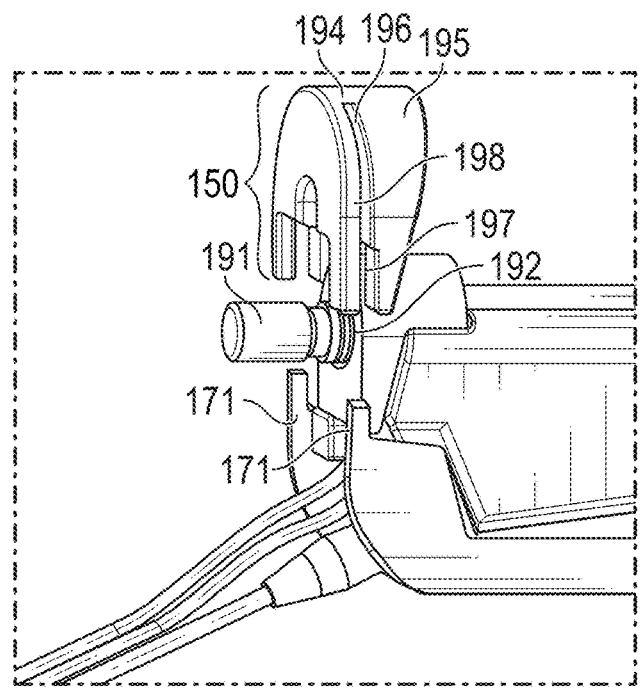
FIG. 11 shows the instrument locking key prior to its engagement with the instrument shaft and lever component of the endoscope handle, in accordance with implementations of the disclosure.
Figure 12:
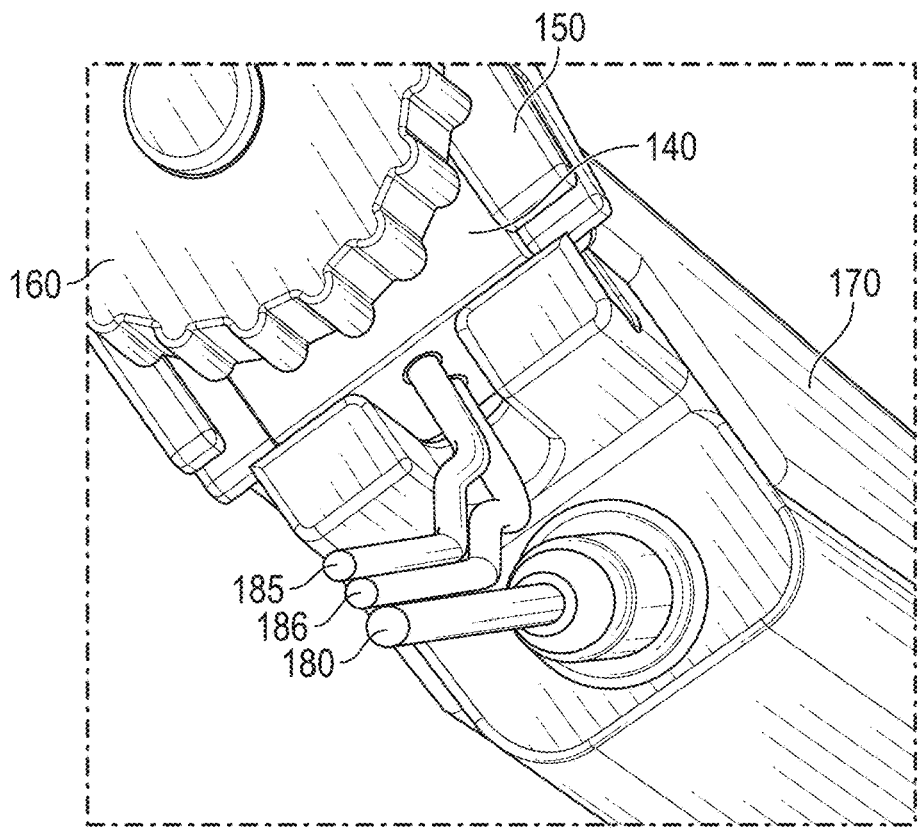
FIG. 12 shows a bottom view of the optical cannula system of FIG. 1 highlighting the streamlined nature of the endoscope cord and suction/irrigation hoses as they exit the device, in accordance with implementations of the disclosure.
Figure 13:
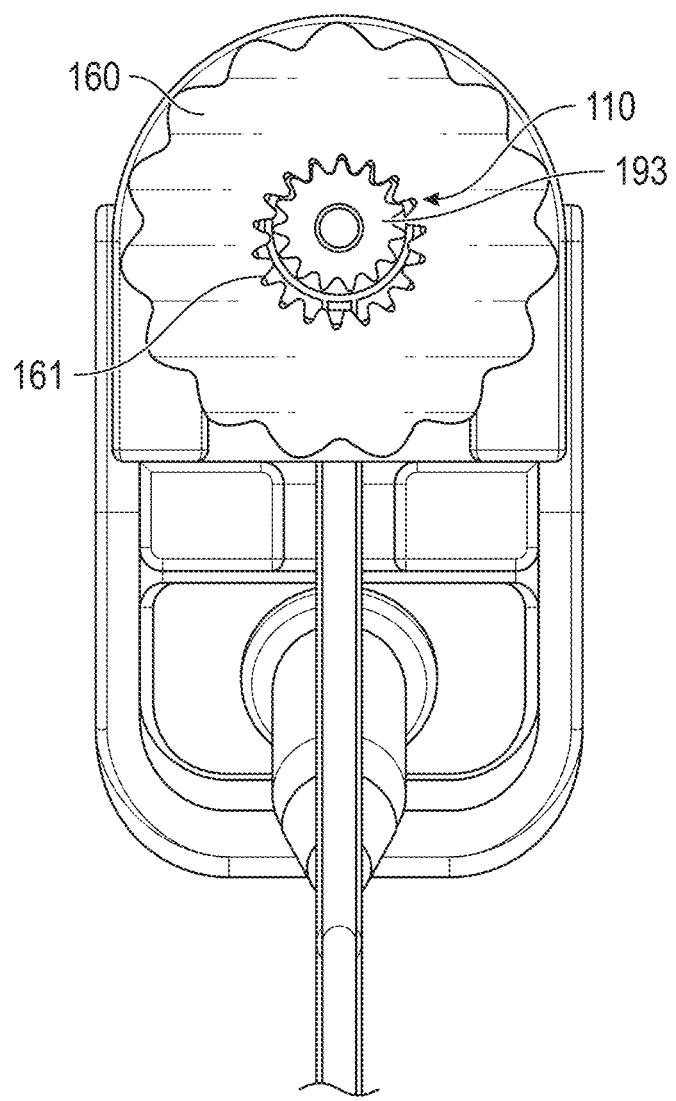
FIG. 13 shows a coronal, cut-away rear view of the optical cannula system of FIG. 1.
Figures 14, 15:
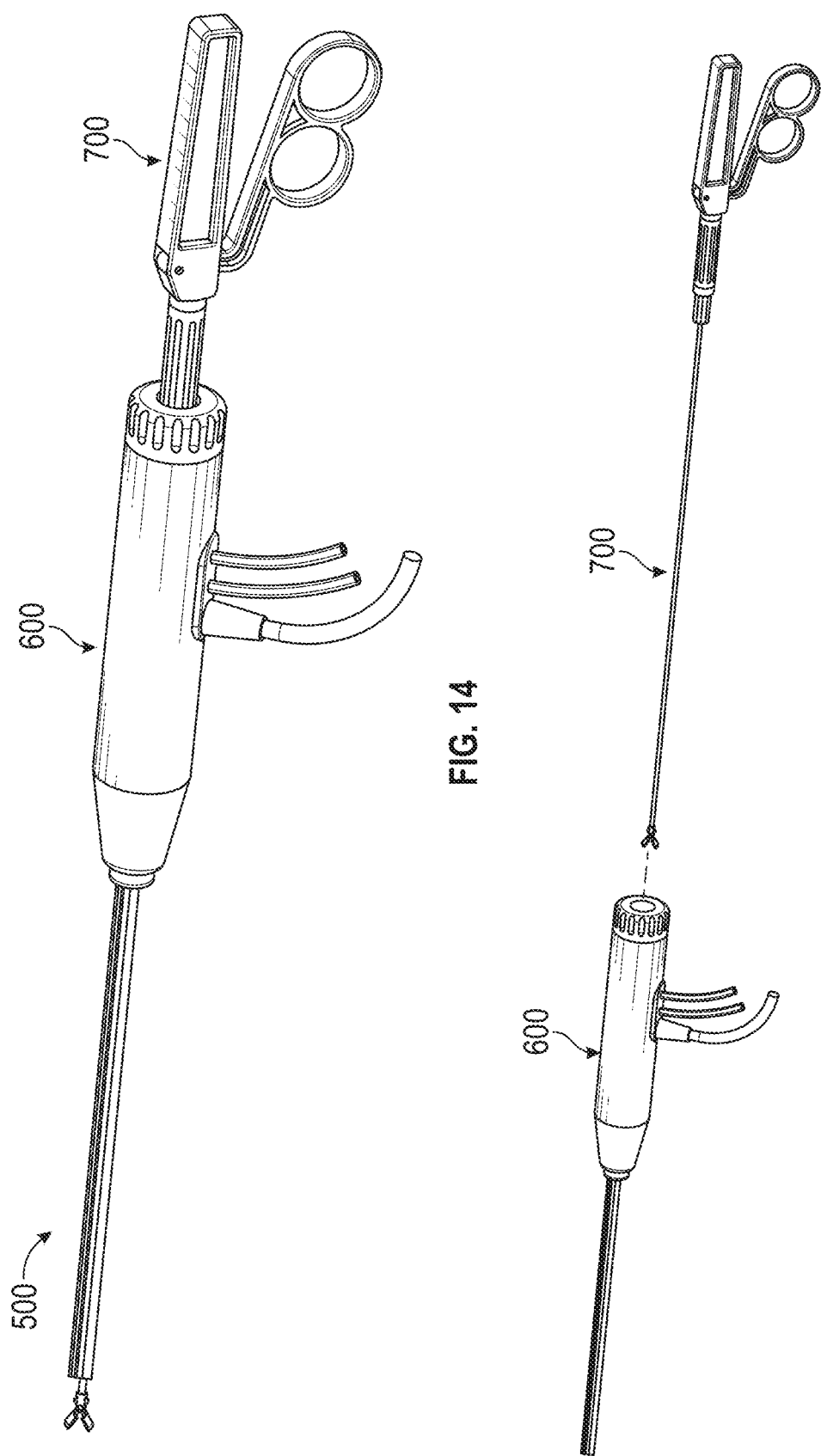
FIG. 14 illustrates another embodiment of an optical cannula system.
FIG. 15 shows the optical cannula system of FIG. 14 including an endoscope and a tool.
Figure 16:
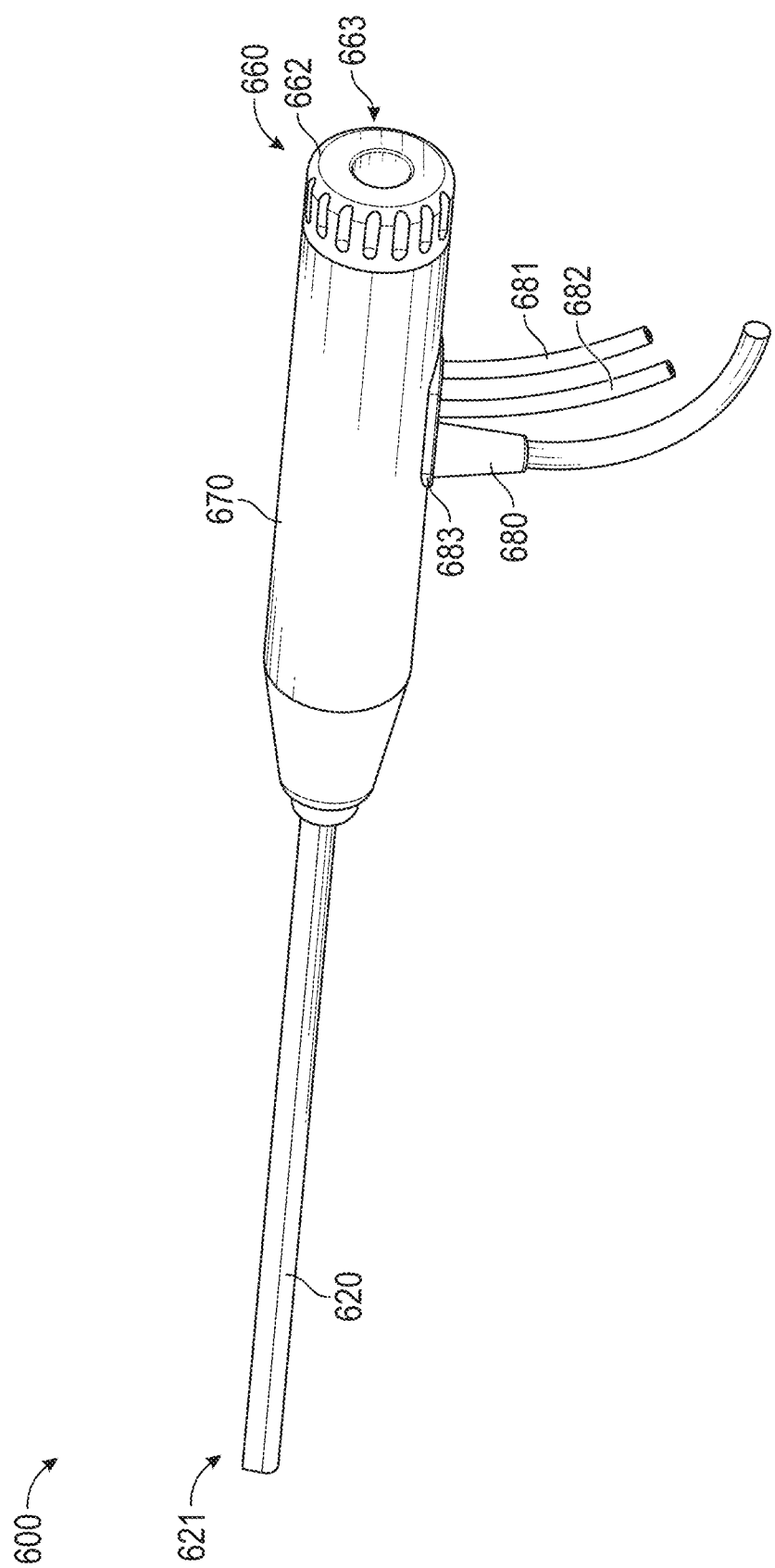
FIG. 16 shows the endoscope of the optical cannula system of FIG. 14.
Figure 17:
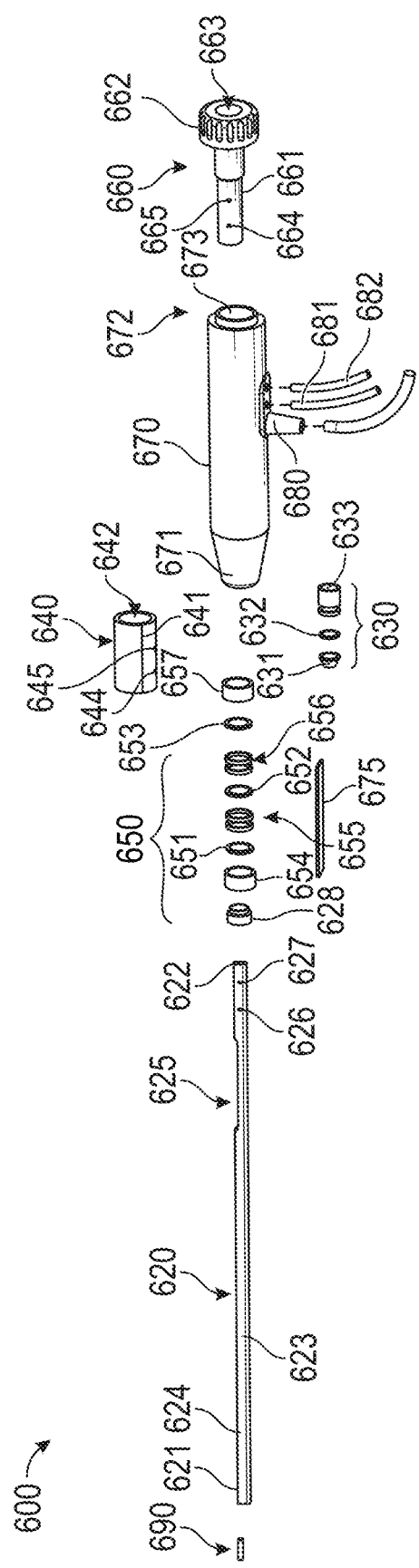
FIG. 17 shows an exploded view of the endoscope of FIG. 16.
Figure 19:
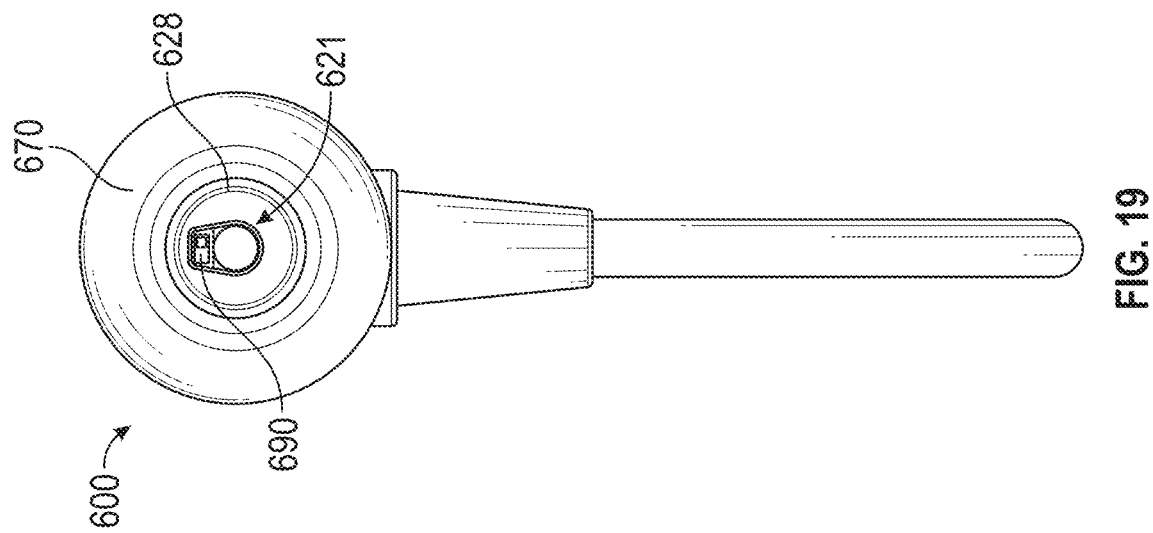
FIG. 19 shows a front view of the endoscope of FIG. 16.
Figure 18:
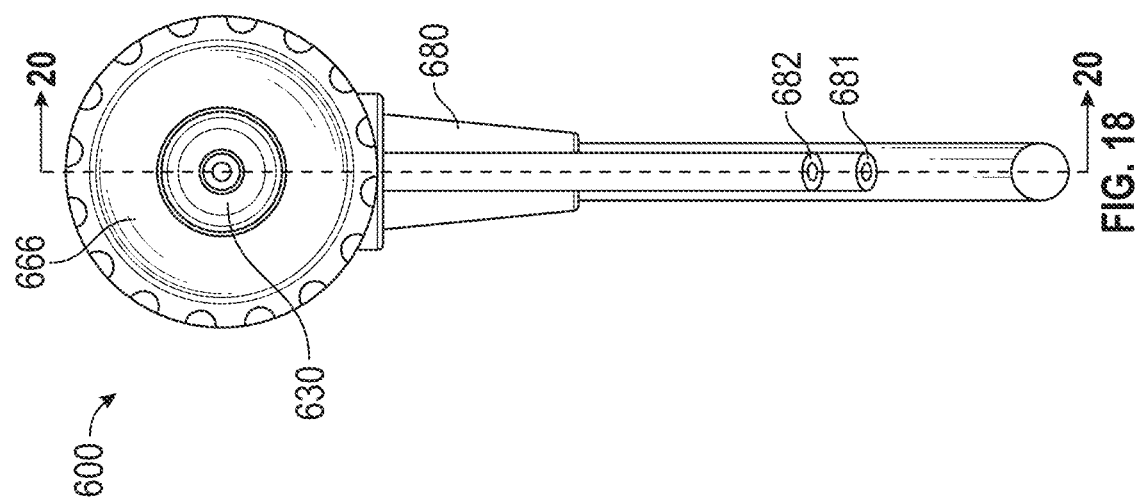
FIG. 18 shows a rear view of the endoscope of FIG. 16.
Figure 20:
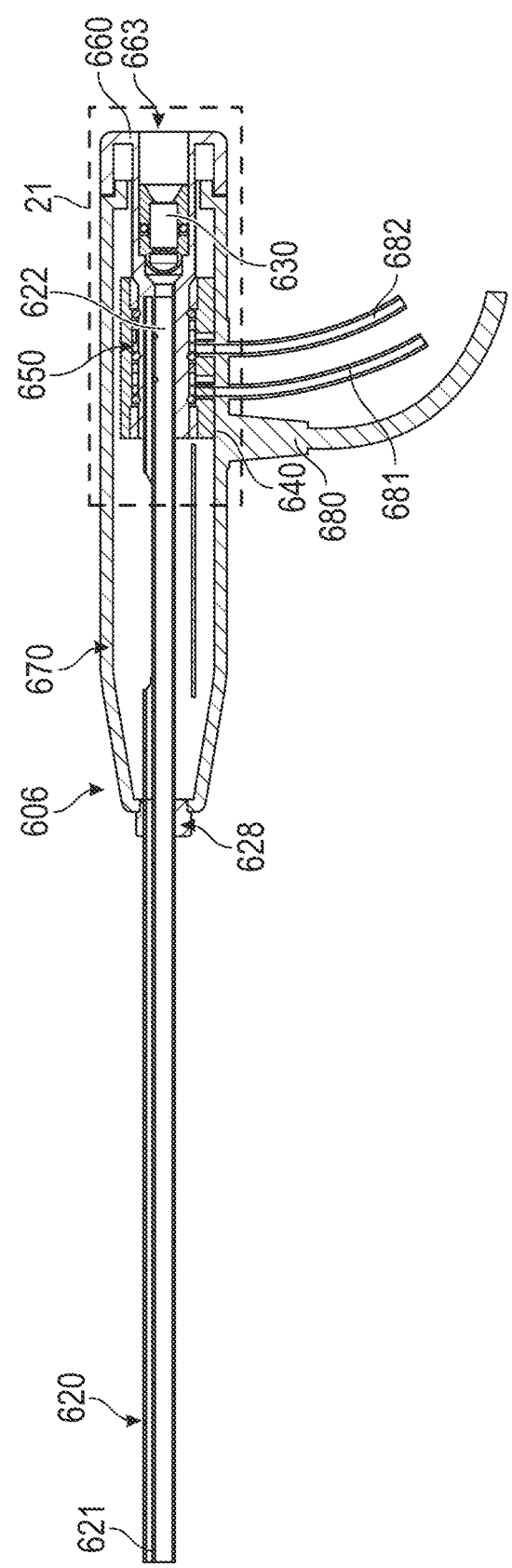
FIG. 20 shows a section view taken on the line 20-20 in FIG. 18.

FIG. 11 shows an instrument shaft protruding out the proximal end of the optical cannula. In this implementation, the back end of the inner shaft 191 has an enlarged posterior extension attached to the inner instrument shaft component. The implementation diagramed in FIG. 13, shows this widened shaft segment fashioned into a gear type configuration 193. Such a configuration would facilitate precise rotation of the instrument shaft 110 within the cannula 120. In these and other envisioned implementations, the gear teeth 193 located on the back end of the instrument shaft 110 could integrate with gear teeth 161 located within the central opening of a rotatable, instrument shaft turn dial 160. The ability to independently rotate the instrument shaft and corresponding tool tip in a manner independent from the position of the optical camera chip (which itself is independently rotatable) would provide surgeons expanded visualization capabilities beyond that offered by traditional arthroscopic systems. Additionally, the ability to load instrument shafts with tool tips that are larger or otherwise configured in a manner that inhibit passing through a cannula inner diameter, expands the tool options available to the surgeon. Adding articulation capabilities to the cannula would even further improve surgical access and visualization especially when combined with the other features of the disclosed system.

Just distal to segment 191 is a segment of instrument shaft containing a small circumferential central groove 192. This groove is embedded into the contour of the outer instrument shaft component 110. FIG. 11 highlights a removable instrument shaft locking key 150. The key is shown prior to engagement with the instrument shaft and bilateral endoscope handle lever extensions 171. The locking key interacts with the instrument shaft, suction/irrigation harness, endoscope handle, and handle lever extensions in a manner that secures all items into position along the back end of the endoscope handle. The locking key 150 has front 195 and back 198 sections connected by a semi-flexible bridge 194 and separated by a slot 196. This bridge 194 acts as a tension hinge to allow the front and back components of the locking key to spread apart from one another. When the locking key is fully engaged, lever extensions 171 project into gaps 197 within the lower sides of the locking key.

When the instrument lever 175 is squeezed against the endoscope handle 170, the superior most aspect of the lever extensions rotate counterclockwise along the pivot point thereby displacing the back section of the locking key 198 away from the front section 195. In this implementation, the front section 195 of the locking key is fixed into position against the irrigation/suction harness, outer instrument shaft, and endoscope handle while the back section of the locking key only engages the proximal shaft extension 191. Counterclockwise movement of the back segment of the locking key causes the inner instrument shaft to move posteriorly in relation to the outer instrument shaft thus activating the distal tool tip mechanism.

FIGS. 14-32 illustrate an optical cannula system 500. The optical cannula system 500 can include the structures and functionalities as the optical cannula system 100 as shown and described in relation to FIGS. 1-13 with the differences noted below. The optical cannula system 500 can include an endoscope 600 and a surgical tool 700. The endoscope 600 can provide physical access to a surgical site for the surgical tool 700, visual images, irrigation, suction and/or other surgical functionalities. The surgical tool 700 can be insertable and removable from the endoscope 600. Although illustrated as a pair of grippers, the tool 700 can include any of a variety of different surgical tools. Alternatively, the tool 700 includes cutting tools, debriding tools, grasping tools, grinding tools, cauterizing tools, drilling tools, tissue sampling tools or other types of surgical tools.

The endoscope 600 can include a body 670, a cannula 620, a rotation mechanism 660, an entry hub 683, an electrical cable 680, a first tube 681, and/or a second tube 682. The body 670 can include a distal end 671 and proximal end 672. The proximal end 672 can include an aperture providing access through an outer wall into an interior 673. The body 670 be generally cylindrically shaped between the distal end 671 and the proximal end 672. The distal end 671 can be tapered toward the cannula 620. The body 670 can include the entry hub 683. The electrical cable 680, the first tube 681 and/or the second tube 682 can enter into the body 670 through the entry hub 683. The electrical cable 680, the first tube 681 and/or the second tube 682 can extend outwardly in a parallel manner to prevent excessive interference or tangling when the endoscope 600 is in use. The electrical cable 680 can be removably coupled or permanently coupled with the entry hub 683.

The cannula 620 can include a distal end 621 and a proximal end 622. The cannula 620 can extend along an axis between the distal end 621 and the proximal end 622. The cannula 620 can have an outer wall that extends from the distal end 621 to the proximal end 622. The outer wall can have a cross-sectional shape extending from the distal end 621 to the proximal end 622. The cannula 620 can include a first channel 623. The first (working) channel 623 can extend from the proximal end 622 to the distal end 621. The cannula 620 can include a second channel 624. The second channel 624 can extend from the proximal end 622 to the distal end 621. An inner wall 629 can separate the first channel 623 from the second channel 624. The inner wall 629 can extend from the proximal end 622 to the distal end 621. The first and second channels 623, 624 can have substantially the same cross-sectional shapes from the proximal end 622 to the distal end 621. The second channel 624 may include a cutout section 625. The cutout section 625 can extend along a portion of the proximal end 622 (e.g., within the body 670). The cannula 620 can comprise a metal alloy, medical grade polymer, or other material. In certain examples, the cannula 620 can comprise a polyether ether ketone (PEEK), liquid crystal polymer (LCP) material, carbon-reinforced nylon, glass-reinforced nylon, or other composite material. The cannula 620 can comprise a unitary structure of a single material.

The cannula 620 can include a first port 626. The first port 626 can be through an outer wall of the cannula 620. The first port 626 can be in communication with the first channel 623. A second port 627 can be spaced from the first port 626. The second port 627 can extend through the outer wall of the cannula 620. The second port 627 can be in communication with the first channel 623. The first and second ports 626, 627 can extend through both sides of the outer wall of the cannula 620. Alternatively, the first and second apertures 626, 627 can each extend through one side of the outer wall of the cannula 620, which can be on opposite sides of the first channel 623 (e.g., the first port 626 can be located on a first side of the outer wall and the second port 627 can be located on the opposite side of the outer wall). In another alternative the first and/or second ports 626, 627 can be in communication with the second channel 624. The first and second ports 626, 627 can each extend through one side of the outer wall of the cannula 620, which can be on opposite sides of the second channel 624. In another alternative, the first port 626 is in communication with the first channel 623 and the second port 627 is in communication with the second channel 624.

The proximal end 622 of the cannula 620 can be received within the interior 673 of the body 670 through the distal end 671. The distal end 621 can protrude from the distal end 671. The cutout section 625 can be within the body 670. The distal end 671 can include an aperture for receiving the cannula 620.

The endoscope 600 can include a forward seal 628. The forward seal 628 can be formed of an elastic material. Forward seal 628 can include a central aperture. The central aperture can be sized to receive the cannula 620 and seal against the outer wall thereof. The seal 628 can include a portion that is at least partially received within the distal end 671. The forward seal 628 can provide a liquid-tight seal between the cannula 620 and an inner wall of the central aperture and between the portion and the distal end 671 of the body 670.

The rotation mechanism 660 can include a dial portion 662, an insertion portion 661, and/or an aperture 663. The dial portion 662 can have a circumferential outer perimeter. The dial portion 662 can have a diameter similar to or greater than a diameter of the body 670 at the proximal end 672. The insertion portion 661 can be cylindrical in shape. The insertion portion 661 can extend in a distal direction from the dial portion 662. A distal end of the insertion portion 661 can have a reduced diameter relative to a proximal portion of the insertion portion 661. An aperture 663 can extend through the dial portion 662 and the insertion portion 661. The aperture 663 can include an inner wall sized to receive the proximal end 622 of the cannula 620. The insertion portion can include a first aperture 664 and a second aperture 665 spaced from the first aperture 664. The first and second apertures 664, 665 can extend through the outer wall of the insertion portion 661 to provide communication within the aperture 663.

The rotation mechanism 660 can be assembled with the body 670. The rotation mechanism 660 can be assembled with the proximal portion 672 of the body 670. The insertion portion 661 can be inserted within the interior space 673. The dial 662 can abut the proximal end 672. The rotation mechanism 660 can be rotatable relative to the body 670, similar to the dial 160 of the system 100. The proximal end 622 of the cannula 620 can be received within the insertion portion 661. The proximal end 622 of the cannula 620 can be rotationally fixed with the insertion portion 661 such that rotation of the dial 662 rotates the cannula 620. The apertures 664, 665 can align with and/or be in communication with the ports 626, 627 of the cannula 620, respectively.

Figure 32:
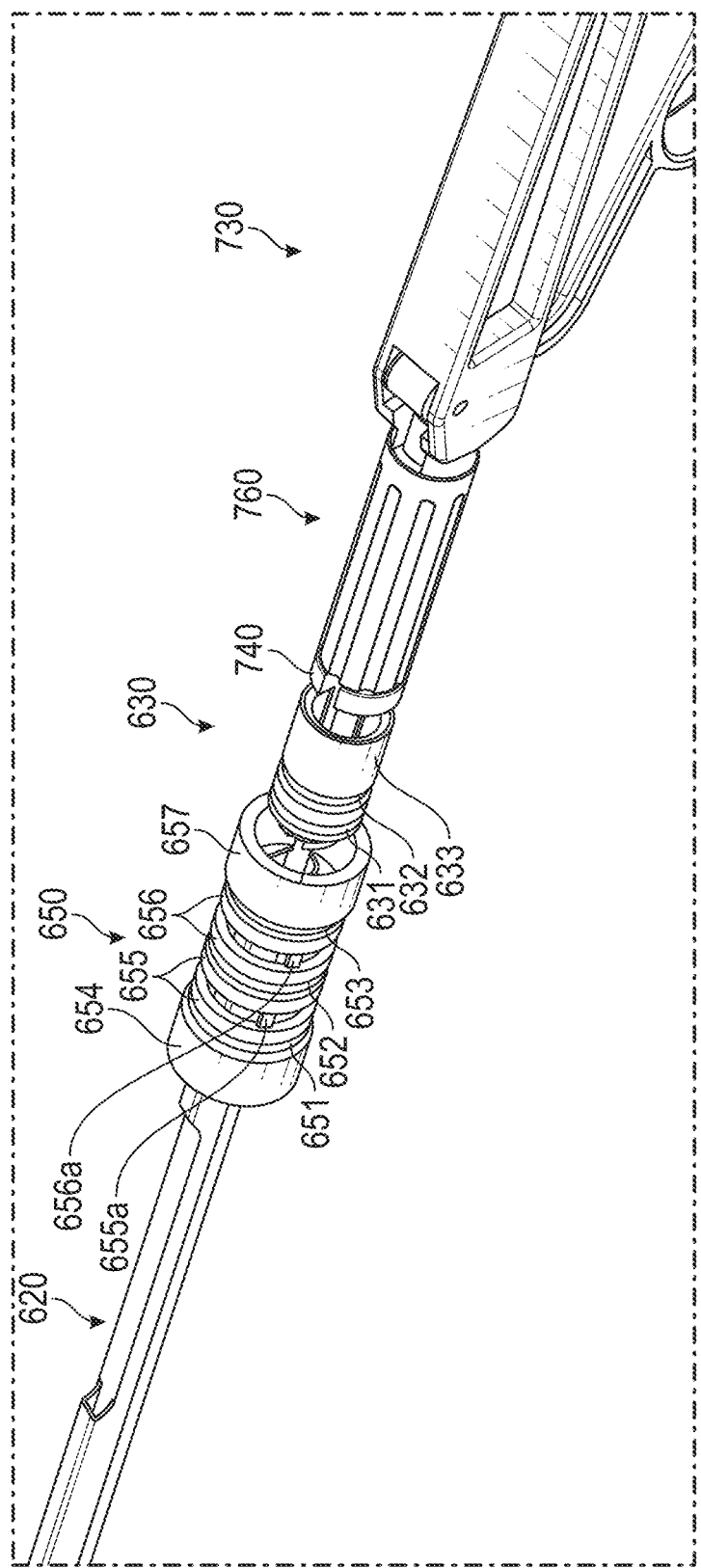
FIG. 32 shows the optical cannula system of FIG. 14 with the body, a harness block, and a rotation member of the endoscope removed for clarity.

The endoscope 600 can include a harness assembly 650. The harness assembly 650 can provide communication between the tubes 681, 682 and the cannula 620, including when rotated. The harness assembly 650 can include a plurality of spacers and seals that are configured to create one or more circumferential pathways for providing irrigation and/or suction to the cannula 620 (e.g., through the respective first and second ports 626, 627 as will be discussed further below). The harness assembly 650 can include first, second, and/or third seals 651, 652, 653. The seals 651-653 can be in the form of O-rings. The harness assembly 650 can include a first spacer 654, a second spacer 655, a third spacer 656, and/or a fourth spacer 657. The first and fourth spacers 654, 657 can be cylindrical in shape. The second and third spacers 655, 656 can include dual rings that are spaced apart by extension members 655a, 656a (FIG. 32). Circumferential fluid pathways 658, 659 (FIG. 21) can be located between the dual rings created by the extension bars. A central aperture can extend through the harness assembly. The central aperture can extend through the first, second, and third seals 651, 652, 653 and the first, second, third, and fourth spacers 654, 655, 656, 657.

The endoscope 600 can include a harness block 640. The harness block 640 can fit around the harness assembly 650 to form the circumferential pathways 658, 659. The harness block 640 can a central aperture 642. The central aperture 642 can have an inner diameter and inner surface. The harness assembly 650 can be assembled within the central aperture 642. The seals 651, 652, 653 can engage with the inner surface of the central aperture 642. The harness block 640 can include a tab portion 641. The tab portion 641 can be located on one side of the harness block 640 to provide a noncylindrical cross-sectional shape thereto (i.e., to prevent rotation within the body 670). A first aperture (port) 644 can extend through an outer wall of the harness block 640 and provide fluid communication with the central aperture 642. A second aperture (port) 645 can be spaced from the first aperture 644 and extend through the outer wall and provide fluid communication with the central aperture 642.

The endoscope 600 can include a tool seal 630. The tool seal 630 can include a first seal 631. The first seal 631 can include flaps or slits that can pass a shaft of a tool therethrough. The tool seal can include a seal body 633. The seal body 633 can be a cylindrically shaped member with an aperture therethrough (e.g., sized to receive the tool shaft). The seal body 633 can include a circumferential recess 633a. The recess 633a can be sized to fit an O-ring 632. The O-ring 632 can be assembled within the recess 633a. A proximal end of the seal body 633 can include a tapered recess opening. In some implementations, the tool seal 630 may be configured to be reversible.

The endoscope 600 can include a camera assembly 690. The camera assembly 690 may include a camera chip like the camera chip 200 and/or additional camera chips. The camera assembly 690 can include a light source (e.g., LED or fiberoptic filament). The camera assembly 690 can be assembled within the distal tip 621 of the cannula 620, such as within the second channel 624. A signal wire (not shown) can extend along the channel 624 between the distal end 621 and the cutout section 625 within the second channel 624. The wire can be attached with an electronic controller (PCB board) 675 within the body 670 (or otherwise connect with the electrical cable 680). The controller 675 can include image processing capabilities and/or other functions. The connection between the signal wire and the electronic controller board 675 can be through a service loop, electrical commutator, or other means.

Figure 21:
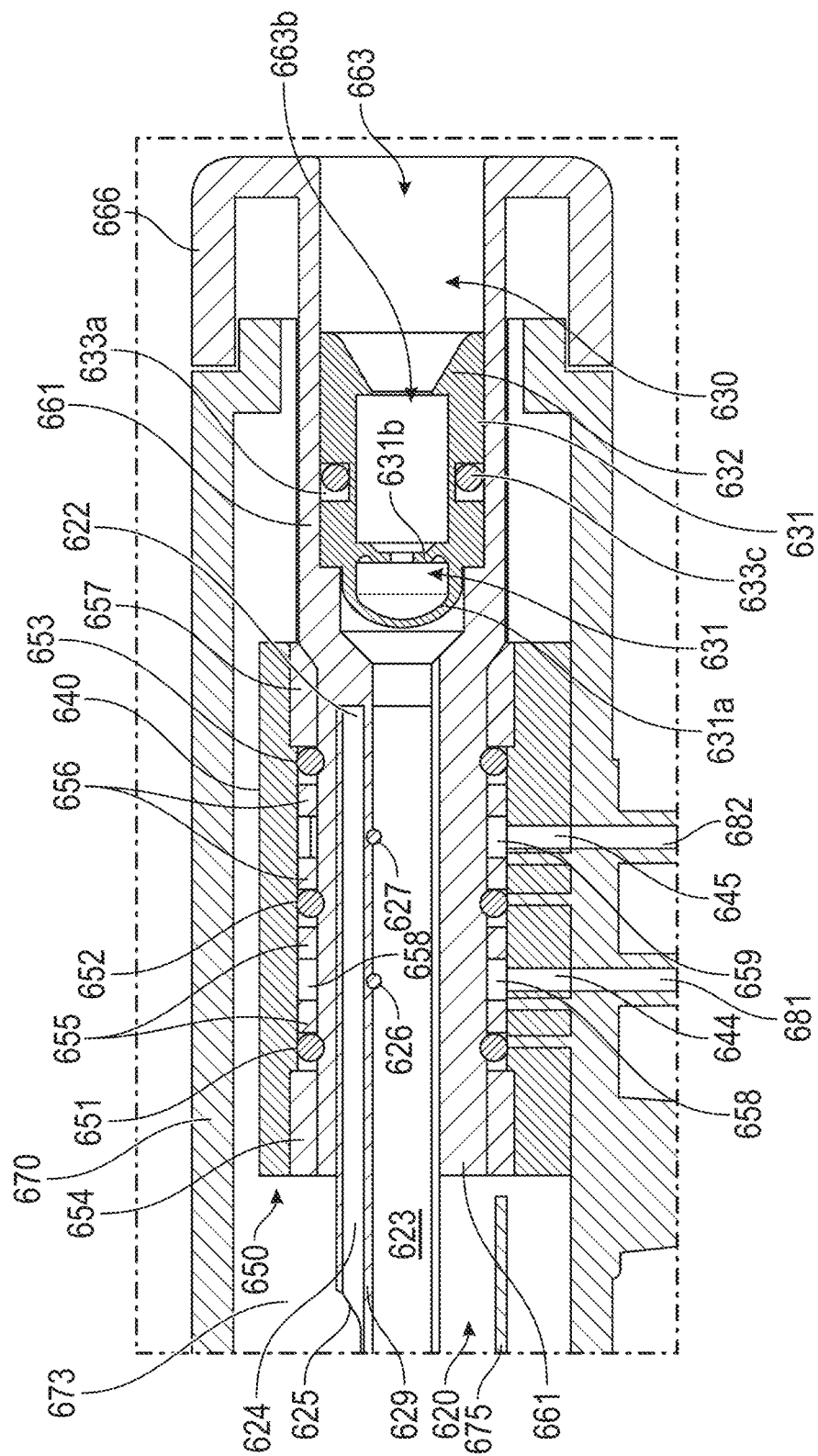
FIG. 21 shows a detail of FIG. 20.
Figure 22:
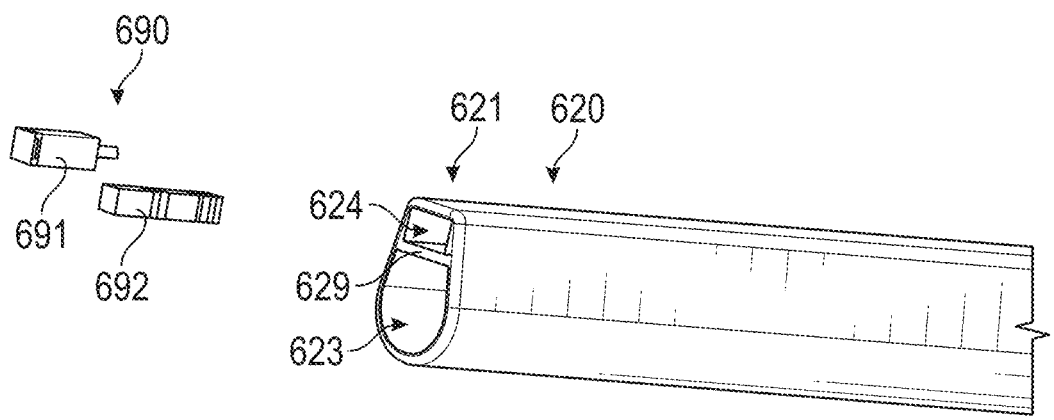
FIG. 22 shows a distal tip of a cannula of the endoscope of FIG. 16.

FIGS. 21-22 show the internal assembly of the endoscope 600. FIG. 21 shows a detail 21 of FIG. 20. The harness block 640 can be assembled within the interior space 673. The tab 641 can engage an inner surface of the body 670 to prevent rotation of the harness block within the body 670. The harness assembly 650 can be assembled within the interior space or aperture 642 of the harness block 640. The interior space 673 can be shaped such that the harness block 640 is in a fixed position (i.e., rotationally) within the interior space 673 such that the harness block 640 is fixed to the body 670. The first aperture 644 can be aligned with and in fluid communication with the first tube 681 through an outer wall of the body 670. The second aperture 645 can be aligned with and in communication with the second tube 682 through the outer wall of the body 670.

The harness assembly 650 is assembled within the central aperture 642 of the harness block 640. The first seal 651 can be located between the first spacer 654 and the second spacer 655. The second seal 652 can be located between the second spacer 655 and the third spacer 656. The third seal can be located between the third spacer 656 and the fourth spacer 657. First spacer 654 can be located on a distal end of the harness assembly 650. The fourth spacer 657 can be located on a proximal end of the harness assembly 650. The second spacer member 655 can form a circumferential fluid pathway 658. The third spacer 656 can form a circumferential fluid pathway 659. The seals 651, 652, 653 can contact the inner surface of the harness block 640 to isolate the pathways 658, 659 from each other. The circumferential pathways 658, 659 can align with and/or be in fluid communication with the respective apertures 644, 645 of the harness block 640. Thereby the circumferential pathways 658, 659 can align with and/or be in fluid communication with the respective tubes 681, 682.

The rotation mechanism 660 can be assembled with the body 670. The insertion portion 661 can be inserted into the central passage of the harness assembly 650 through the proximal end 672. The seals 651, 652, 653 can contact the outer surface of the insertion portion 661 to isolate the pathways 658, 659 from each other. The first and second apertures (ports) 664, 665 can align with and be in fluid communication with the respective circumferential pathways 658, 659.

The proximal end 622 and the cannula 620 can be received within the interior space 673 such as through the distal end 671. The distal end 622 can be received within the insertion portion 661. The aperture 664 of the rotation mechanism 660 can be aligned with and/or in fluid communication with the first port 626 of the cannula 620. Accordingly, the first tube 681, aperture 644, circumferential pathway 658, aperture 664, and port 626 can be in fluid communication. The aperture 665 of the rotation mechanism 660 can be aligned with and/or in fluid communication with the second port 627 of the cannula 620. Accordingly, the second tube 682, aperture 645, circumferential pathway 659, aperture 665, and port 627 can be in fluid communication.

The insertion portion 661 can be rotatable along a longitudinal axis thereof (e.g., by rotating the dial 662). The cannula 620 can be locked into rotation with the rotation mechanism 660. The rotation mechanism 660 can rotate relative to the harness assembly 650, the harness block 640, and/or the body 670. Rotation of the insertion portion 661 within the harness assembly 650 can maintain alignment and/or fluid communication between the apertures of the cannula 620 and the tubes 681, 682 through the circumferential pathways 658, 659. Rotation of the insertion portion 661 within the harness assembly 650 can be at least 90° or 360° and optionally unlimited (e.g., for a commutator).

The shaft seal 630 can be inserted into the insertion portion 661 through the aperture 663. The shaft seal 630 can be a uni-directional seal. The shaft seal 630 can be inserted into the aperture 663 through the proximal end of the rotation assembly 660. The shaft seal 630 and aperture 663 can aligned with the first channel 623. The shaft seal 630

(e.g., the O-ring 632) can seal against an inner surface of the aperture 663. A tapered portion of the insertion portion 661 can provide a seat for the seal 630. The shaft seal 630 can be inserted into a proximal portion of the insertion portion 661. The first seal 631 can include a first seal member 631a and a second seal member 631b. The first seal member 631a can include a dome shape. The second seal member 631b can attach with the first seal member 631a. The first and/or second seal members 631a, 631b can include a central aperture or slit therethrough. Optionally, the shaft seal 630 can be inserted in the reverse orientation as illustrated in FIG. 21 (e.g., to accommodate distal-to-proximal loading on an instrument shaft within the cannula). In an alternative embodiment, a rotatable or switchable lever can be included that couples with shaft seal 630. The lever can switch between uni-directional seals (e.g., to accommodate distal-to-proximal loading on an instrument shaft within the cannula or differently sized seals) and/or provide an option for no seal at all depending on the instrument inserted into the handle.

Figure 23:
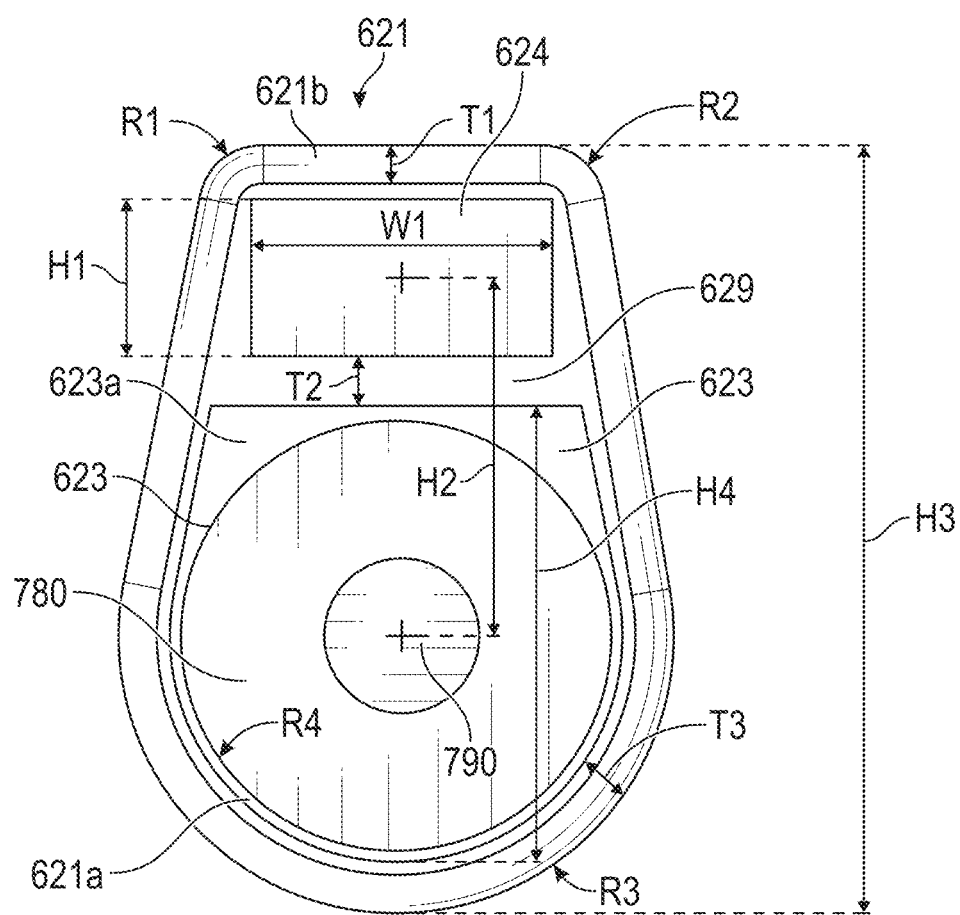
FIG. 23 shows a front view of the distal tip of a cannula of the endoscope of FIG. 16 including a shaft of the tool within a working channel.
Figure 24:
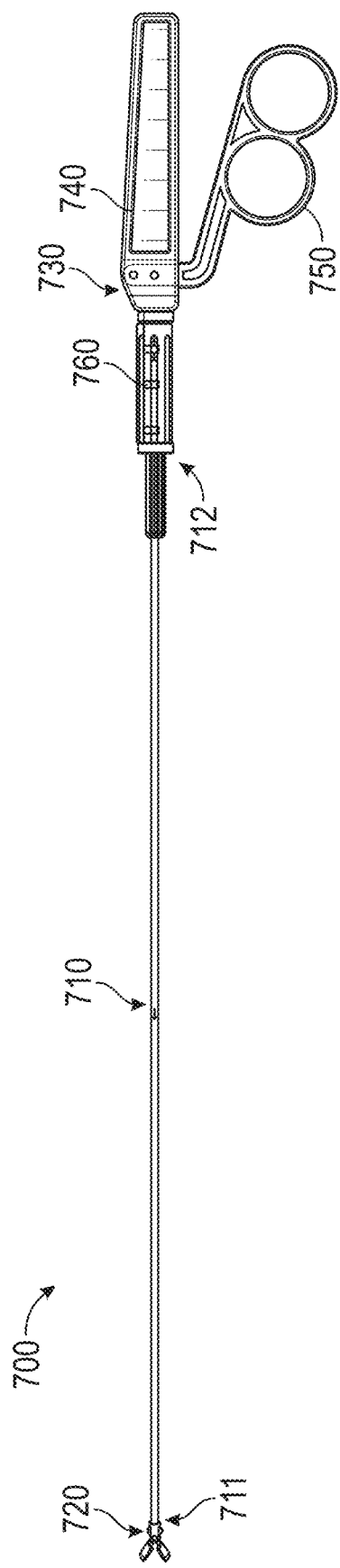
FIG. 24 shows a tool of the optical cannula system of FIG. 14.
Figure 25:
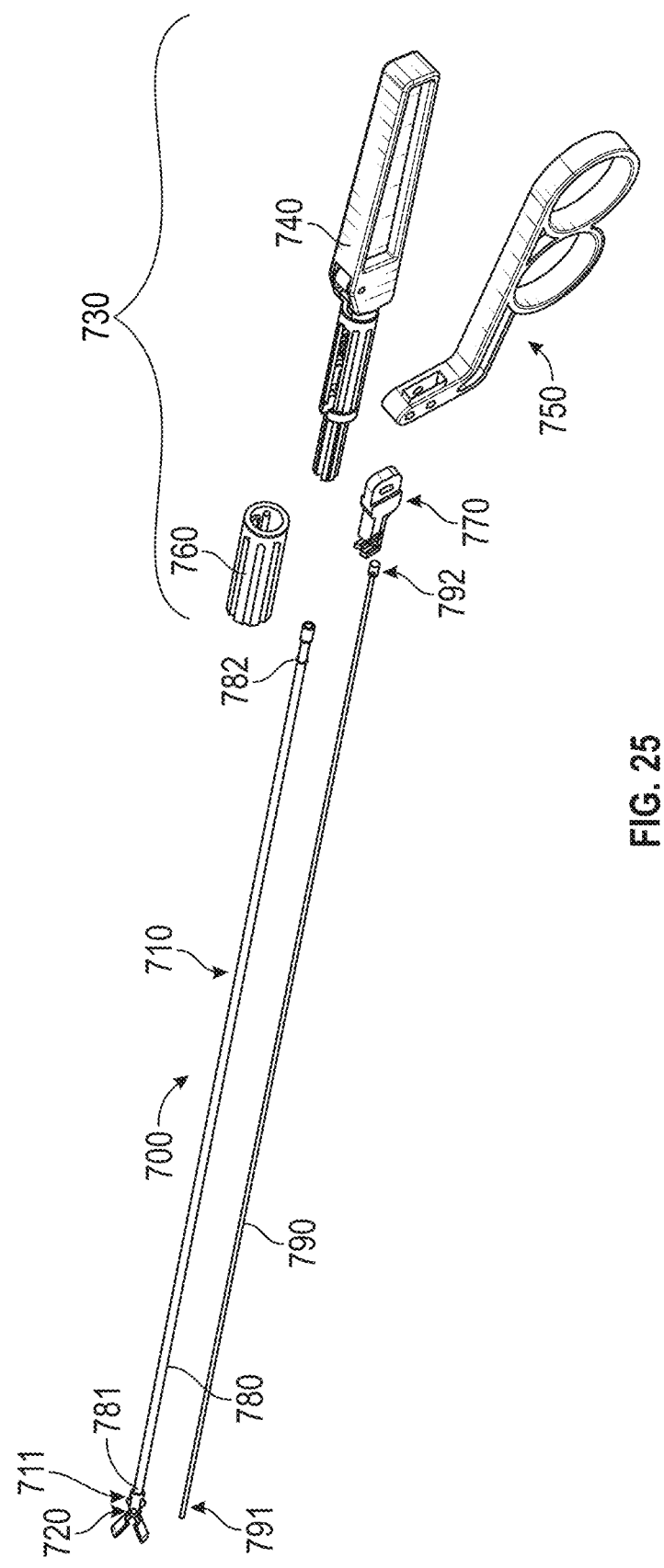
FIG. 25 shows an exploded view of the tool of FIG. 24.
Figure 26:
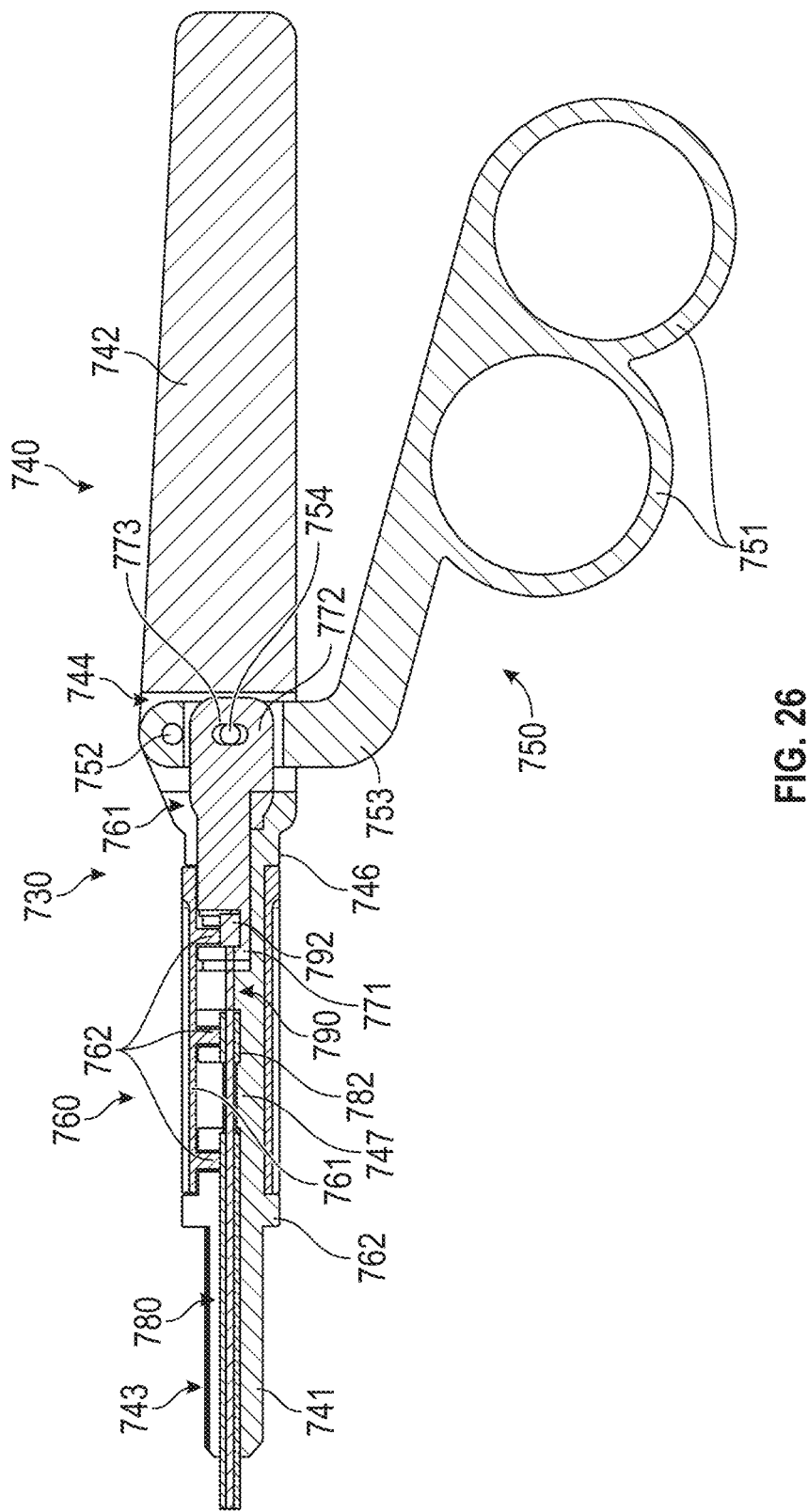
FIG. 26 shows a section view of a grip portion of the tool of FIG. 24.

FIGS. 22-23 shows the distal end 621 of the cannula 620 including the first channel 623 and the second channel 624 that are within an interior space defined by an outer wall of the cannula 620. The outer wall of the cannula 620 can include a curved or circular lower portion 621a. The outer wall of the cannula 620 can include a flat or upper portion 621b. The curved portion 621a can be attached with the flat portion 621b on either side through curved or planar side portion. The first channel 623 can be located within the curved lower portion 621a. Additionally, the first channel 623 can include a first side portion 623a and a second side portion 623b. Optionally, the first and second side portions 623a, 623b can in use be at least partially separated. The first channel 623 can be sized to receive a shaft 710 of the tool 700. The shaft 710 can include an outer shaft 780 and an inner shaft 790. The first channel 623 can be sized such that the shaft 710 generally fills the channel 623. Suction and irrigation can occur along the first and second side portion 623a, 623b or otherwise around the shaft 710. Optionally, the channel 623 and the shaft 710 can be sized such that shaft 710 separates the first side portion 623a from the second side portion 623b which can be located in upper opposite corners of the first channel 623. In one alternative, the first side portion 623a can be aligned with the first port 626 and the second side portion 623b can be aligned with the second port 627 such that irrigation can occur along the first side portion 623a and suction can occur independently along the second side portion 623b.

An inner wall 629 separates the first channel 623 from the second working channel 624. The inner wall 629 can extend from the proximal end 622 to the distal end 621. Alternatively, additional inner walls can be included to further divide the interior space of the cannula 620. The second channel 624 can have a rectangular or trapezoidal cross-sectional shape. The shape of the second channel 624 can be sized such that the camera assembly 690 fits within the distal end of the second channel 624. Alternatively additional camera chips or lights or other instruments can be fit within the second channel 624. The camera assembly 690 can include a camera chip 691 and a light source 692. The first channel 623 can have an arched cross-sectional shape with a circular portion and a flat portion. The outer wall of the cannula 620 can have a thickness T1 between the flat portion 621b and the second channel 624. The outer wall of the cannula 620 can have a first upper rounded edge R1 and an a second upper rounded edge R2. A third curvature R3 can extend below the first channel 623. An inner portion of the outer wall within the first channel 623 can have a curvature R4. The second channel have a height H1 and/or a width W1. The inner wall 629 can have a thickness T2. The outer wall between the third curvature R3 and the fourth curvature R4 can have a thickness T3. The second channel 624 can be spaced from the first channel 623 by a height H2. The outer wall of the cannula 620 can have a height H3 (e.g., center-line-to-centerline). The first channel 623 can have a height H4. The chart below provides certain desirable values and ranges for the dimensions of the cannula 620. Alternatively, other cannula and channel dimensions are within the scope of the present disclosure.

|  | Dimension (mm) | Dimension Range (mm) |
| --- | --- | --- |
| R1/R2 | 0.5 | 0.1-3.0 |
| R3 | 4.4 | 2.5-8.0 |
| R4 | 3.6 | 2.0-7.0 |
| T1/T2/T3 | 0.4 | 0.1-4.0 |
| H1 | 1.3 | 0.5-4.0 |
| W1 | 2.4 | 0.5-8.0 |
| H2 | 2.8 | 0.5-8.0 |
| H3 | 6.1 | 4.0-12.0 |
| H4 | 3.6 | 2.0-9.0 |

FIGS. 24-27 show the tool 700 in further detail. The tool 700 can include the shaft 710 with a tool 720 on a distal end 711 of the shaft 710. A proximal end 712 of the shaft 710 can be attached with a grip assembly 730. The grip assembly 730 can include a grip body 740, a lever 750 and/or an assembly sleeve 760.

The shaft 710 can include an outer shaft 780. The outer shaft 780 can include a distal end 781 and a proximal end 782. The distal end 781 can attach with the tool assembly 720. The proximal end 782 can include a proximal portion including a shoulder that aids in assembly with the grip portion 730.

The shaft 710 can include an inner shaft 790. The inner shaft 790 can be a control mechanism for the tool 720. The inner shaft 790 can include a distal end 791. The distal end 791 can be connected with the tool 720 such as for actuating a pair of grippers. A proximal end 792 can be attached with the grip assembly 730 (e.g., the lever 750) for purposes of actuation.

The grip body 740 with a distal portion 741 and a proximal portion 742. The distal portion 741 can include a general cylindrical shape with a slot 743 extending from the distal end proximally towards the proximal portion 742. The slot 743 can provide access for assembling the shaft 710 with the grip portion 730. The distal portion 741 can include a distal flange 745. The slot 743 can extend through the distal flange 745. A proximal flange 746 can be located proximal to the distal flange 745. The grip body 740 can include a slot 744 for receiving one end of the grip level 750. The distal portion 741 can include a shoulder or recess 747. The shoulder or recess 747 can engage with the shoulder of the proximal end 782 of the outer shaft 780. The shoulder or recess 747 can be aligned with the slot 743 or accessible therethrough.

The grip assembly 730 can additionally include a catch member 770. The catch member 770 can include a distal end with a catch 771. The catch 771 can be configured to engage the proximal end 791 of the inner shaft 790. The catch 771 can be aligned with the slot 743 or accessible therethrough. The catch member 770 can include a proximal end 772. The proximal end 772 can include a slot 773. The catch member 770 can be assembled within the grip body 740 and held in place by the assembly sleeve 760. The catch member 770 can be attached our coupled with the lever 750 for providing actuation of the inner shaft 790. The proximal end of the inner shaft 790 can include a shoulder for attachment of the catch 771.

The lever 750 can include a grip portion 751 that may include one or more finger holes. The lever 750 can include a shaft portion 753 that includes a pivot 752. Pivot 752 can attach the lever 750 within the slot apertures 744. The lever 750 can be pivotally connected at the pivot 752. Alternatively, the lever 750 can be integrally formed with the grip body 740 (e.g., a living hinge). The lever 750 can include a pin 754. The pin 754 can engage within a slot 773 on a proximal end 772 of the catch member 770. The movement of the lever 750 can move the catch member 770 axially in line with the shaft 710.

Figure 27:
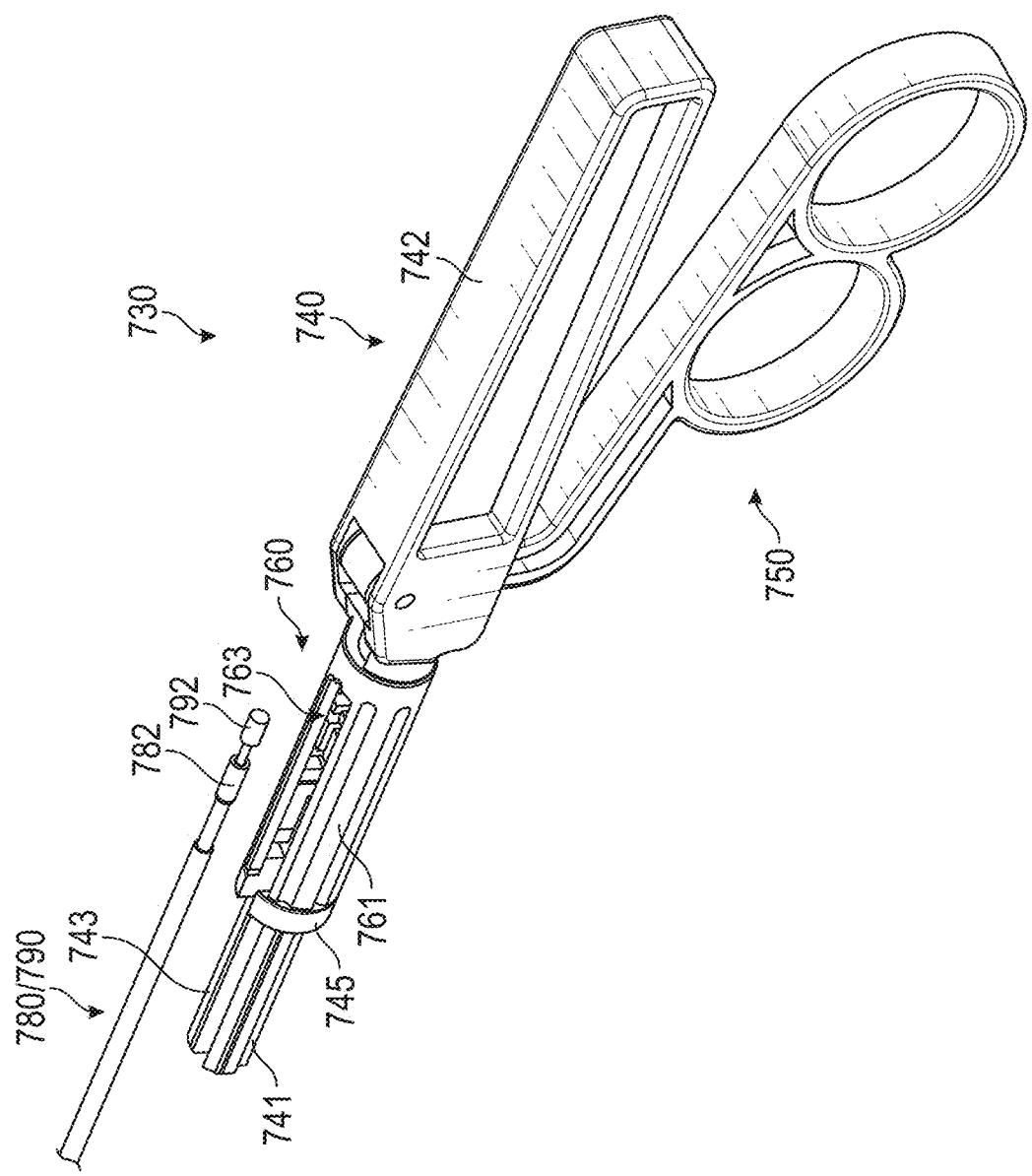
FIG. 27 shows the grip portion of the tool in an open configuration for assembling and disassembling a shaft of the tool.

The assembly sleeve 760 can be assembled between the distal flange 745 and the proximal flange 746. The assembly sleeve 760 can be rotatable about the distal portion 741 of the grip body 740. The assembly sleeve 760 can be rotatable into and out of an assembly configuration in which a slot 763 of the assembly sleeve 760 aligns with the slot 743 on the grip body 740. The shafts 780, 790 can be assembled through the slot 743 when the slot 763 in the assembly configuration (FIG. 27). This can also provide for a quick assembly and disassembly configuration for the tool 700. After the shafts 780, 790 have been inserted within the slot 743, the assembly sleeve 760 can be rotated to move the assembly slot 763 and cover the slot 743. This can lock the proximal ends 782, 792 into place within the grip assembly 730.

Figure 28:
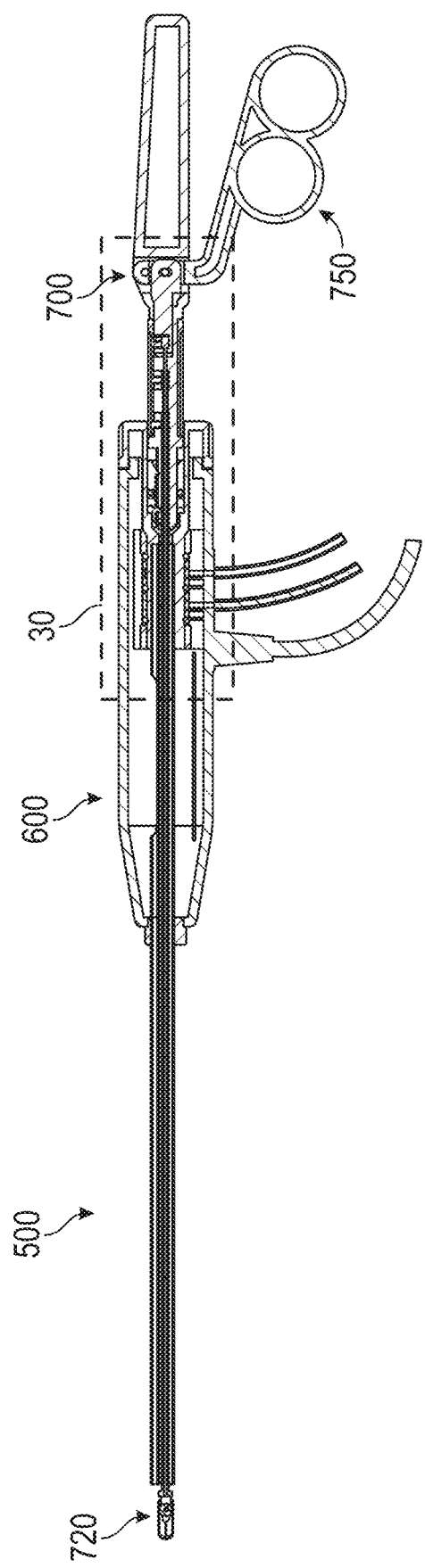
FIG. 28 shows a section view of optical cannula system of FIG. 14 in a first configuration.
Figure 29:
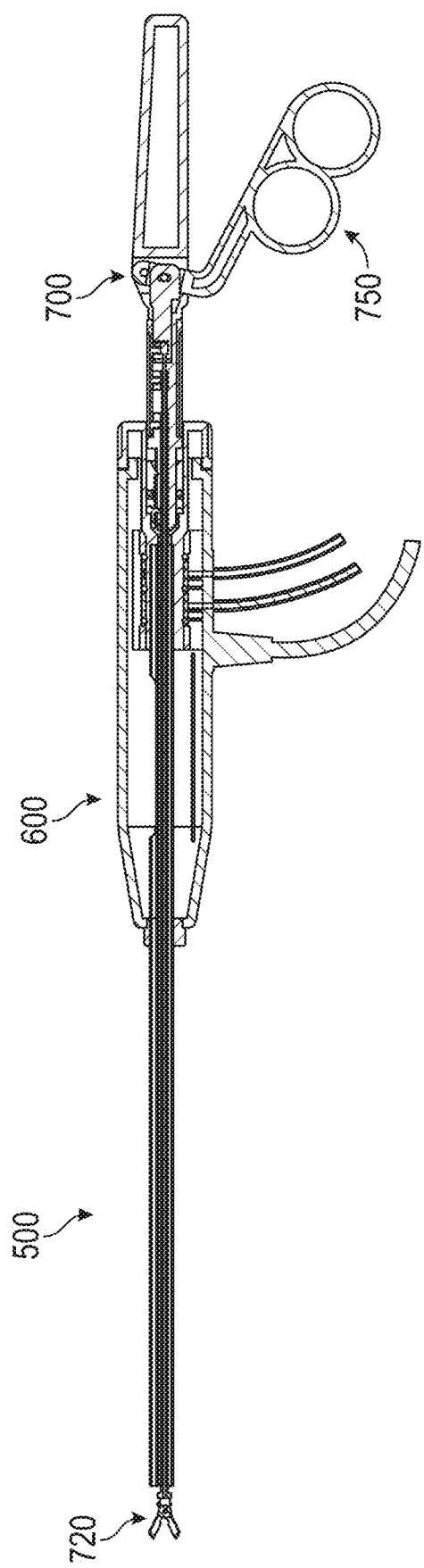
FIG. 29 shows a section view of optical cannula system of FIG. 14 in a second configuration.
Figure 30:
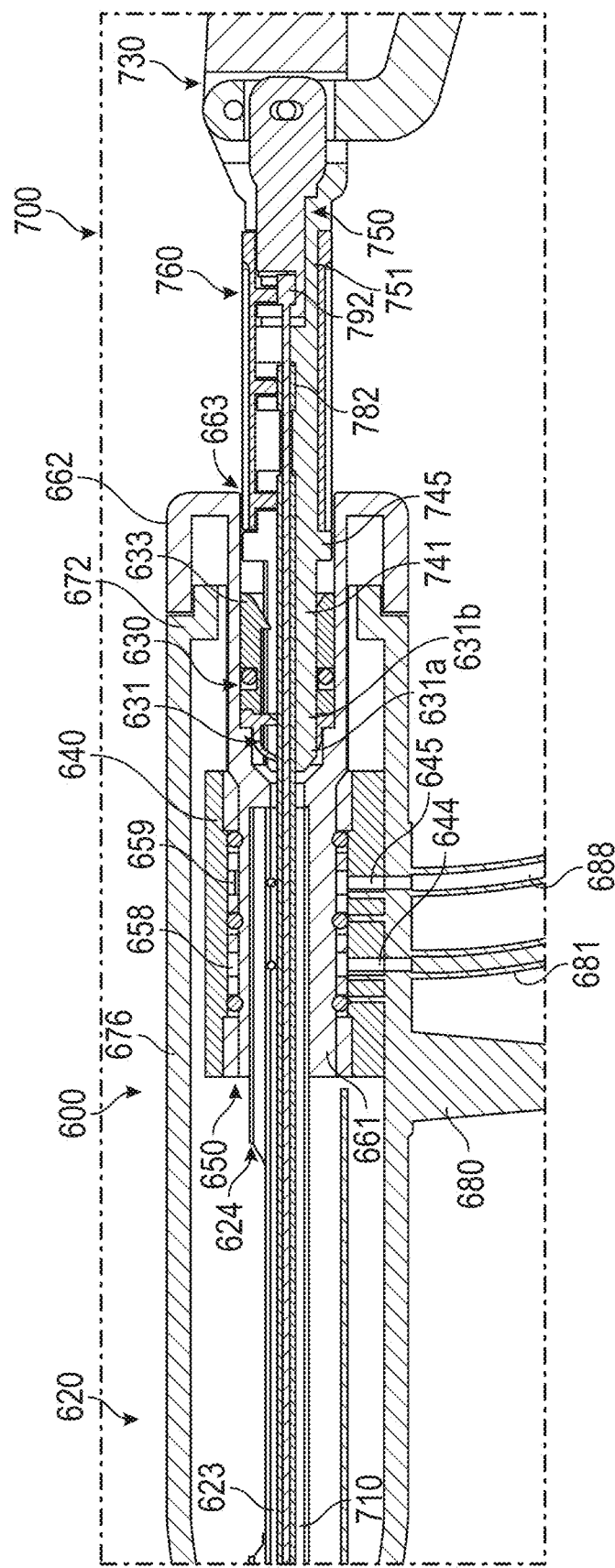
FIG. 30 shows a detail of FIG. 28.
Figure 31:
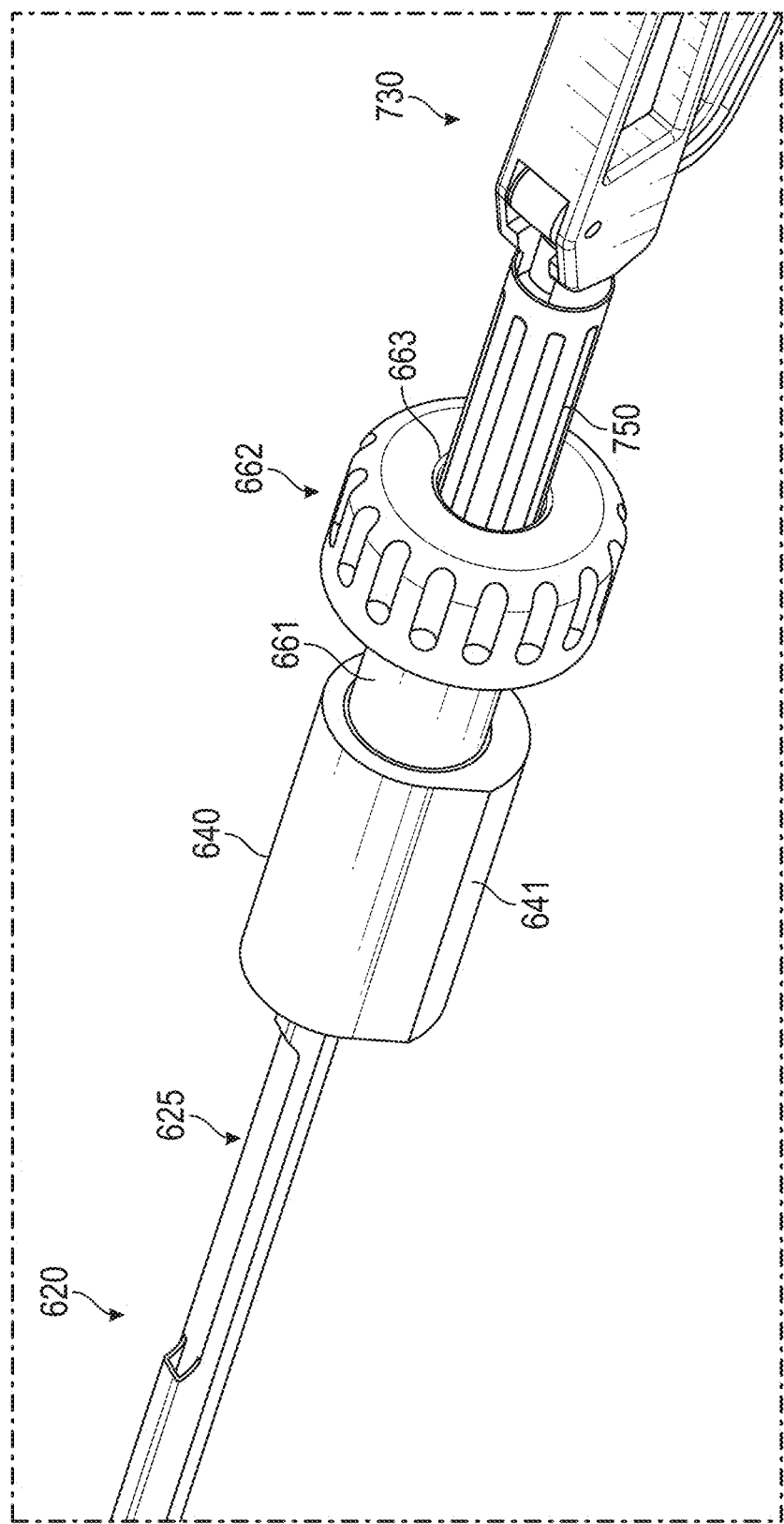
FIG. 31 shows the optical cannula system of FIG. 14 with a body of the endoscope removed for clarity.

FIGS. 28-32 illustrates assembly the optical cannula system 500 with the tool 700 received within the endoscope 600. FIG. 28 shows a first configuration with the jaws of the tool 720 and a first configuration (closed). FIG. 29 shows the tool 720 in a second configuration with the jaws open. The lever 750 having been actuated to advance the catch member 770 and actuate the jaws through the shaft 790. FIG. 30 shows a detail 30 of FIG. 28.

The shaft 710 is received within the cannula 620. When loaded proximally to distally, the shaft is inserted through the rotation mechanism 660 (e.g., aperture 663) and into the first channel 623 of the cannula 620. The shaft 710 can be inserted through the shaft seal 630. The seal member 631 of the seal 630 can seal against the passage of fluid back through the aperture 663. The first seal 631 can seal around the shaft 710. The first seal 631 can be positioned distally relative to the body 633.

When loaded distally-to-proximally, the tool 700 can be at least partially disassembled. The shaft 710 is inserted within the proximal end 712 entering the distal end 621 of the cannula 620. The shaft seal 630 can be removed from the aperture 663 and replaced in the reverse orientation. The proximal end 712 can be loaded into the rotation mechanism 660 (e.g., aperture 663) from the first channel 623 of the cannula 620. The shaft 710 can be inserted through the shaft seal 630. The seal member 631 of the seal 630 can seal against the passage of fluids back through the aperture 663. The first seal 631 can seal around the shaft 710. The first seal 631 can be positioned proximally relative to the body 633. The shaft 710 can then be reassembled with the grip assembly 730. Alternatively, to reversing the seal 630, a second seal in the reverse orientation can be installed within the aperture 633.

The distal portion 741 of the tool 700 can be received at least partially within the aperture 663. The aperture 663 can include a length such that the distal portion 741 can be inserted to varying depths within the aperture 663 while still being engaged with the rotation mechanism 660. In this manner, the tool portion 720 can be moved relative to the cannula 620 (e.g., the tool portion 720 can be extended and retracted relative to the distal end 621). Optionally, the distal portion 741 can be sized such that the tool 700 can be rested within the rotation mechanism 660. In this configuration, the tool 700 can rotate with the rotation mechanism 660. In this configuration, the surgeon can free one hand to attend to other tasks while the endoscope 600 and tool 700 are held in the other hand. Otherwise, the tool 700 can be rotated or otherwise moved independent of the cannula 620.

Certain Terminology

Terms of orientation used herein, such as "top," "bottom," "proximal," "distal," "longitudinal," "lateral," and "end," are used in the context of the illustrated example. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain examples include or do not include, certain features, elements, and/or steps. Thus, such conditional language is not generally intended to imply that features, elements, and/or steps are in any way required for one or more examples.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

The terms "approximately," "about," and "substantially" as used herein represent an amount close to the stated amount that still performs a desired function or achieves a desired result. For example, in some examples, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain examples, as the context may dictate, the term "generally parallel" can refer to something that departs from exactly parallel by less than or equal to 20 degrees. All ranges are inclusive of endpoints.

SUMMARY

Several illustrative examples of optical cannula systems have been disclosed. Although this disclosure has been described in terms of certain illustrative examples and uses, other examples and other uses, including examples and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various examples. All possible combinations and subcombinations of elements and components described herein are intended to be included in this disclosure. No single feature or group of features is necessary or indispensable.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a subcombination.

Any portion of any of the steps, processes, structures, and/or devices disclosed or illustrated in one example in this disclosure can be combined or used with (or instead of) any other portion of any of the steps, processes, structures, and/or devices disclosed or illustrated in a different example or flowchart. The examples described herein are not intended to be discrete and separate from each other. Combinations, variations, and some implementations of the disclosed features are within the scope of this disclosure.

While operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in some implementations. Also, the separation of various components in the implementations described above should not be understood as requiring such separation in all implementations, and it should be understood that the described components and systems can generally be integrated together in a single product or packaged into multiple products. Additionally, some implementations are within the scope of this disclosure.

Further, while illustrative examples have been described, any examples having equivalent elements, modifications, omissions, and/or combinations are also within the scope of this disclosure. Moreover, although certain aspects, advantages, and novel features are described herein, not necessarily all such advantages may be achieved in accordance with any particular example. For example, some examples within the scope of this disclosure achieve one advantage, or a group of advantages, as taught herein without necessarily achieving other advantages taught or suggested herein. Further, some examples may achieve different advantages than those taught or suggested herein.

Some examples have been described in connection with the accompanying drawings. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various examples can be used in all other examples set forth herein. Additionally, any methods described herein may be practiced using any device suitable for performing the recited steps.

For purposes of summarizing the disclosure, certain aspects, advantages and features of the inventions have been described herein. Not all, or any such advantages are necessarily achieved in accordance with any particular example of the inventions disclosed herein. No aspects of this disclosure are essential or indispensable. In many examples, the devices, systems, and methods may be configured differently than illustrated in the figures or description herein. For example, various functionalities provided by the illustrated modules can be combined, rearranged, added, or deleted. In some implementations, additional or different processors or modules may perform some or all of the functionalities described with reference to the examples described and illustrated in the figures. Many implementation variations are possible. Any of the features, structures, steps, or processes disclosed in this specification can be included in any example.

In summary, various examples of optical cannula systems and related methods have been disclosed. This disclosure extends beyond the specifically disclosed examples to other alternative examples and/or other uses of the examples, as well as to certain modifications and equivalents thereof. Moreover, this disclosure expressly contemplates that various features and aspects of the disclosed examples can be combined with, or substituted for, one another. Accordingly, the scope of this disclosure should not be limited by the particular disclosed examples described above, but should be determined only by a fair reading of the claims.

The invention claimed is:

1. An optical cannula system, comprising:
   a cannula, comprising:
      a proximal portion;
      a distal end;
      an axis extending between the proximal portion and the distal end;
      an outer cannula wall defining an interior space extending along the axis; and
      an inner cannula wall within the outer cannula wall extending along the axis, the inner cannula wall dividing the interior space into a first channel and a second channel;
   a body configured to receive the proximal portion of the cannula, wherein the cannula is rotatable within the body;
   a first camera chip positioned at the distal end within the second channel;
   a harness, comprising:
      an inner surface disposed about the proximal portion of the cannula;
      a first circumferential seal disposed between the outer cannula wall and the inner surface of the harness;
      a second circumferential seal disposed between the outer cannula wall and the inner surface of the harness, the second circumferential seal spaced from the first circumferential seal to define a first fluid channel between the outer cannula wall and the inner surface; and
      a first harness port in fluid communication with the first fluid channel; and a first cannula port disposed through the outer cannula wall into the interior space, wherein the first fluid channel is in fluid communication with the interior space through the first cannula port.

2. The optical cannula system of claim 1, the harness further comprising:
a third circumferential seal disposed between the outer cannula wall and the inner surface of the harness, the third circumferential seal spaced from the second circumferential seal to define a second fluid channel between the outer cannula wall and the inner surface;
a second harness port in fluid communication with the second fluid channel; and
a second cannula port disposed through the outer cannula wall into the interior space,
wherein the second fluid channel is in fluid communication with the interior space through the second cannula port.

3. The optical cannula system of claim 2, wherein the first and second fluid channels are in fluid communication with the respective first and second cannula ports during rotation of the cannula relative to the harness.

4. The optical cannula system of claim 3, wherein:
the harness is rotationally fixed within the body; and
the first and second cannula ports are in fluid communication with respective first and second hoses through the first and second fluid channels and the first and second harness ports.

5. The optical cannula system of claim 4, wherein:
the harness includes a harness block, the harness block comprising:
a central aperture defined by the inner cannula wall; and
the first and second harness ports,
wherein the harness block is rotationally fixed within the body.

6. The optical cannula system of claim 5, further comprising:
an insertion portion attached with a rotation mechanism, the insertion portion positioned between the outer cannula wall and the first, second and third circumferential seals of the harness such that the first and second fluid channels are positioned between an outer wall of the insertion portion and the inner surface of the harness block,
wherein the insertion portion includes first and second insertion portion ports aligned with the respective first and second fluid channels, and wherein the first and second cannula ports are in fluid communication with the first and second hoses during rotation of the cannula relative to the harness through the first and second fluid channels, the first and second harness ports, and the first and second insertion portion ports.

7. The optical cannula system of claim 6, wherein the insertion portion is attached with a dial of the rotation mechanism and configured to rotate the cannula relative to the body.

8. The optical cannula system of claim 4, wherein the first and second hoses depart the body in a parallel configuration.

9. The optical cannula system of claim 4, wherein the first hose is an irrigation hose and the second hose is a suction hose.

10. The optical cannula system of claim 9, wherein the first and second cannula ports are in fluid communication with the first channel of the cannula.

11. The optical cannula system of claim 10, wherein an instrument shaft is disposed within the first channel and divides a first side of the first channel from a second side of the first channel, the first cannula port is in communication with the first side of the first channel and the second cannula port is in communication with the second side of the first channel.

12. The optical cannula system of claim 9, wherein the first and second cannula ports are in fluid communication with the second channel of the cannula.

13. The optical cannula system of claim 9, wherein the first cannula port is in communication with the first channel of the cannula and the second cannula port is in communication with the second channel of the cannula.

14. The optical cannula system of claim 1, further comprising:
a camera signal wire within the second channel connected with the first camera chip, the camera signal wire being electrically connected with an electrical coupler by a service loop or electrical commutator; and
an external electrical cable including an external coupler configured to electrically connect with the electrical coupler,
wherein the cannula, the first camera chip, the harness and any attached tubes, the external electrical cable, and the external coupler are removable from the body such that the body can be reusable.

15. The optical cannula system of claim 1, further comprising:
a camera signal wire within the second channel connected with the first camera chip, the camera signal wire being electrically connected with an electronic control board within the body by a service loop or electrical commutator, the electronic control board coupled with an external electrical cable.

16. The optical cannula system of claim 1, further comprising:
a turn dial engaged with the outer cannula wall and configured to transmit a torque to the cannula.

17. The optical cannula system of claim 1, further comprising:
a second camera chip positioned at the distal end within the second channel, the first camera chip positioned on a first side of the second channel and the second camera chip positioned on a second side of the second channel.

18. The optical cannula system of claim 17, wherein the first and second camera chips are in a divergent orientation to provide different viewing angles.

19. The optical cannula system of claim 17, wherein images from the first and second camera chips digitally combined to create a panoramic field of view and images of the distal end of the cannula are digitally removed or reduced from combined panoramic field of view.

20. The optical cannula system of claim 1, further comprising:
a light source at the distal end of the second channel.

21. The optical cannula system of claim 1, wherein the outer cannula wall of the cannula has a circular cross-sectional shape, the second channel has a crescent cross-sectional shape and the first channel has a circular cross-sectional shape.

22. The optical cannula system of claim 1, wherein the second channel has a rectangular or trapezoidal cross-sectional shape.

23. An optical cannula system, comprising:
a cannula, comprising:
a proximal portion;
a distal end;

an axis extending between the proximal portion and the distal end;

an outer cannula wall defining an interior space extending along the axis; and an inner cannula wall within the outer cannula wall extending along the axis, the inner cannula wall dividing the interior space into a first channel and a second channel;

a body configured to receive the proximal portion of the cannula, wherein the cannula is rotatable within the body;

a first camera chip positioned at the distal end within the second channel;

a tool, comprising:

an instrument shaft configured to be inserted within the interior space of the outer cannula wall, the instrument shaft comprising an inner shaft and an outer shaft;

a surgical tool at a distal end of the instrument shaft, wherein a distal end of the inner shaft is coupled with the surgical tool;

a lever coupled with a proximal end of the inner shaft;

a grip portion attached with the proximal end the instrument shaft, the lever attached with the grip portion; and a catch coupled with the lever, wherein the outer shaft is coupled with the grip portion and the proximal end of the inner shaft is coupled with the catch such that squeezing the lever actuates the surgical tool; and an assembly sleeve including a first slot, wherein the grip portion includes a second slot, and wherein alignment of the first slot with the second slot permits the assembly or disassembly of the outer shaft with the grip portion and the inner shaft with the catch and misalignment of the first slot with the second slot locks the outer shaft within the grip portion and the inner shaft within the catch.

24. The optical cannula system of claim 23, wherein the instrument shaft includes a collar, and the grip portion includes a turn dial, the collar insertable within an aperture of the turn dial such that the instrument shaft rotates with the cannula.

25. The optical cannula system of claim 23, further comprising:

an instrument seal disposed within the grip portion;

wherein the instrument seal includes a central aperture aligned with the first channel of the cannula and configured to receive the instrument shaft.

26. The optical cannula system of claim 25, wherein the instrument seal is removable and reversible to accommodate either distal-to-proximal or proximal-to-distal loading of the instrument shaft.

27. The optical cannula system of claim 23, wherein rotation of the instrument shaft is independent of rotation of the cannula.

28. The optical cannula system of claim 27, wherein the instrument shaft is coupled with a first turn dial for rotating the surgical tool.

29. The optical cannula system of claim 23, further comprising:

a second camera chip positioned at the distal end within the second channel, the first camera chip positioned on a first side of the second channel and the second camera chip positioned on a second side of the second channel.

30. The optical cannula system of claim 29, wherein the first and second camera chips are in a divergent orientation to provide different viewing angles.

31. The optical cannula system of claim 29, wherein images from the first and second camera chips digitally combined to create a panoramic field of view and images of the distal end of the cannula are digitally removed or reduced from combined panoramic field of view.

32. The optical cannula system of claim 23, further comprising:

a light source at the distal end of the second channel.

33. The optical cannula system of claim 23, wherein the outer cannula wall of the cannula has a circular cross-sectional shape, the second channel has a crescent cross-sectional shape, and the first channel has a circular cross-sectional shape.

34. The optical cannula system of claim 23, wherein the second channel has a rectangular or trapezoidal cross-sectional shape.

* * * * *